(12) United States Patent
Dacosta et al.

(10) Patent No.: US 11,123,120 B2
(45) Date of Patent: Sep. 21, 2021

(54) IMPLANTS, ALIGNMENT GUIDES, SYSTEMS AND METHODS OF USE

(71) Applicant: Paragon 28, Inc., Englewood, CO (US)

(72) Inventors: Albert Dacosta, Lone Tree, CO (US); Frank S. Bono, Castle Rock, CO (US); Randy Allard, Golden, CO (US); Richard David Hunt, Arvada, CO (US); Spanky Raymond, Uniontown, OH (US); Laura Zagrocki Brinker, Lone Tree, CO (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 16/509,160

(22) Filed: Jul. 11, 2019

(65) Prior Publication Data

US 2020/0015868 A1 Jan. 16, 2020

Related U.S. Application Data

(63) Continuation of application No. PCT/US2019/041305, filed on Jul. 11, 2019.
(Continued)

(51) Int. Cl.
*A61B 17/80* (2006.01)
*A61B 17/17* (2006.01)
(Continued)

(52) U.S. Cl.
CPC ........ *A61B 17/808* (2013.01); *A61B 17/1728* (2013.01); *A61B 17/8057* (2013.01);
(Continued)

(58) Field of Classification Search
CPC .............. A61B 17/808; A61B 17/8052; A61B 17/8057; A61B 17/8061; A61B 2017/681
See application file for complete search history.

(56) References Cited

U.S. PATENT DOCUMENTS

| 3,709,219 A | 1/1973 | Halloran |
| 5,350,380 A | 9/1994 | Goble |

(Continued)

FOREIGN PATENT DOCUMENTS

| EP | 0617927 | 10/1994 |
| EP | 1273271 | 8/2007 |

(Continued)

OTHER PUBLICATIONS

International Search Report and Written Opinion of the International Searching Authority for PCT/US2019/041305, dated Nov. 12, 2019, 15 pages.

(Continued)

*Primary Examiner* — Christopher D. Prone
(74) *Attorney, Agent, or Firm* — Heslin Rothenberg Farley & Mesiti P.C.; Jacquelyn A. Graff, Esq.

(57) ABSTRACT

Bone fusion system, devices, guide, implant and methods for using the bone fusion system, devices, guide and implant are disclosed. The fusion system includes an alignment guide and an implant. The alignment guide couples to the implant. The alignment guide includes a body, a fixation member engaging a first end of the body, and a tissue protector engaging a second end of the body. The implant includes a body portion, an extension portion extending away from a first end of the body portion, a curved portion extending away from a second end of the body portion, and a foot member extending away from the curved portion perpendicular to the body portion. Finally, methods for using the bone fusion system, devices, guide and implant are disclosed.

19 Claims, 37 Drawing Sheets

Related U.S. Application Data

(60) Provisional application No. 62/696,788, filed on Jul. 11, 2018, provisional application No. 62/811,980, filed on Feb. 28, 2019.

(51) Int. Cl.
*A61B 17/86* (2006.01)
*A61B 17/88* (2006.01)
*A61B 17/68* (2006.01)

(52) U.S. Cl.
CPC ........ *A61B 17/8061* (2013.01); *A61B 17/864* (2013.01); *A61B 17/8897* (2013.01); *A61B 2017/681* (2013.01)

(56) References Cited

U.S. PATENT DOCUMENTS

| | | |
|---|---|---|
| 5,352,228 A | 10/1994 | Kummer |
| 5,458,602 A | 10/1995 | Goble |
| 6,342,057 B1 | 1/2002 | Brace |
| 6,692,496 B1 | 2/2004 | Wardlaw |
| 7,011,665 B2 | 3/2006 | Null |
| 7,785,326 B2 | 8/2010 | Green |
| 7,819,877 B2 | 10/2010 | Guzman |
| 8,206,389 B2 | 6/2012 | Huebner |
| 8,231,627 B2 | 7/2012 | Huebner |
| 9,044,250 B2 | 6/2015 | Olsen et al. |
| 9,161,796 B2 | 10/2015 | Chiodo |
| 9,241,744 B2 | 1/2016 | Blake |
| 9,421,103 B2 | 8/2016 | Jeng et al. |
| 2003/0009217 A1 | 1/2003 | McKeman |
| 2005/0033301 A1 | 2/2005 | Lombardo |
| 2006/0189996 A1 | 8/2006 | Orbay |
| 2007/0173843 A1 | 7/2007 | Matityahu |
| 2007/0225714 A1 | 9/2007 | Gradl |
| 2007/0239168 A1 | 10/2007 | Kuenzi |
| 2007/0265634 A1 | 11/2007 | Weinstein |
| 2007/0270850 A1 | 11/2007 | Geissler |
| 2008/0091197 A1 | 4/2008 | Coughlin |
| 2008/0188852 A1 | 8/2008 | Matityahu |
| 2009/0036931 A1 | 2/2009 | Pech |
| 2009/0088767 A1 | 4/2009 | Leyden |
| 2009/0093849 A1 | 4/2009 | Grabowski |
| 2010/0087824 A1 | 4/2010 | Collazo |
| 2010/0121324 A1 | 5/2010 | Tyber |
| 2011/0046681 A1 | 2/2011 | Prandi et al. |
| 2011/0144700 A1 | 6/2011 | Konieczynski |
| 2011/0218576 A1 | 9/2011 | Galm |
| 2011/0270319 A1 | 11/2011 | Sheffer |
| 2011/0282397 A1 | 11/2011 | Richter |
| 2012/0078252 A1 | 3/2012 | Huebner |
| 2012/0209268 A1 | 8/2012 | Overes |
| 2012/0303038 A1 | 11/2012 | Durante |
| 2013/0046311 A1 | 2/2013 | Blake et al. |
| 2013/0150903 A1 | 6/2013 | Vincent |
| 2013/0325076 A1 | 12/2013 | Palmer |
| 2014/0066996 A1 | 3/2014 | Price et al. |
| 2014/0180348 A1 | 6/2014 | Thoren et al. |
| 2015/0032168 A1 | 1/2015 | Orsak et al. |
| 2015/0150683 A1 | 6/2015 | Donner et al. |
| 2015/0182267 A1 | 7/2015 | Wolf et al. |
| 2015/0245923 A1 | 9/2015 | Abdou |
| 2015/0359580 A1 | 12/2015 | Dacosta et al. |
| 2016/0030064 A1 | 2/2016 | DaCosta et al. |
| 2016/0135858 A1 | 5/2016 | Dacosta et al. |
| 2016/0235414 A1 | 8/2016 | Hatch et al. |
| 2016/0242791 A1 | 8/2016 | Fallin et al. |
| 2016/0310191 A1 | 10/2016 | Seykora |
| 2016/0324552 A1 | 11/2016 | Baker et al. |
| 2016/0354128 A1 | 12/2016 | Jeng |
| 2017/0216043 A1 | 8/2017 | Surma et al. |
| 2018/0110530 A1 | 4/2018 | Wagner et al. |
| 2018/0242987 A1 | 8/2018 | Lintula et al. |
| 2018/0242988 A1 | 8/2018 | Dacosta et al. |
| 2018/0280069 A1 | 10/2018 | Barmes et al. |
| 2019/0015140 A1 | 1/2019 | Dacosta et al. |
| 2019/0038326 A1 | 2/2019 | Hedgeland et al. |

FOREIGN PATENT DOCUMENTS

| | | |
|---|---|---|
| EP | 2745786 | 6/2014 |
| EP | 3023068 | 5/2016 |
| FR | 3030221 | 6/2016 |
| JP | 04250156 | 9/1992 |
| JP | 2009112954 | 5/2009 |
| WO | 19940015556 | 7/1994 |
| WO | 2005089660 | 9/2005 |
| WO | 2009052294 | 4/2009 |
| WO | 2012103335 | 8/2012 |
| WO | 2012106477 | 8/2012 |
| WO | 2013009574 | 1/2013 |
| WO | 2014105750 | 7/2014 |
| WO | 2015094409 | 6/2015 |
| WO | 2017011656 | 1/2017 |
| WO | 2018157170 | 8/2018 |

OTHER PUBLICATIONS

Extended European Search Report (EESR) for EP Application No. 17863986.0, dated Sep. 15, 2020 (13 pages).
Partial Supplementary European Search Report issued in European Patent Application No. 18757770.5 dated Dec. 3, 2020, 11 pages.
Partial Supplementary European Search Report issued in European Patent Application No. 18758239.0, dated Dec. 10, 2020, 11 pages.
European Communication Pursuant to Article 94(3) EPC (Office Action) for EP Application No. 18201132.0 dated Feb. 12, 2021, 5 pages.
Partial Supplementary European Search Report issued in European Patent Application No. 18777784.2, dated Jan. 14, 2021, 13 pages.
Extended European Search Report issued in European Patent Application No. 18757770.5, dated Mar. 9, 2021, 10 pages.
Extended European Search Report issued in European Patent Application No. 18758239.0, dated Apr. 8, 2021, 12 pages.
Extended European Search Report issued in European Patent Application No. 18831633.5, dated Apr. 16, 2021, 10 pages.
Extended European Search Report issued in European Patent Application No. 18777784.2, dated Apr. 16, 2021, 11 pages.

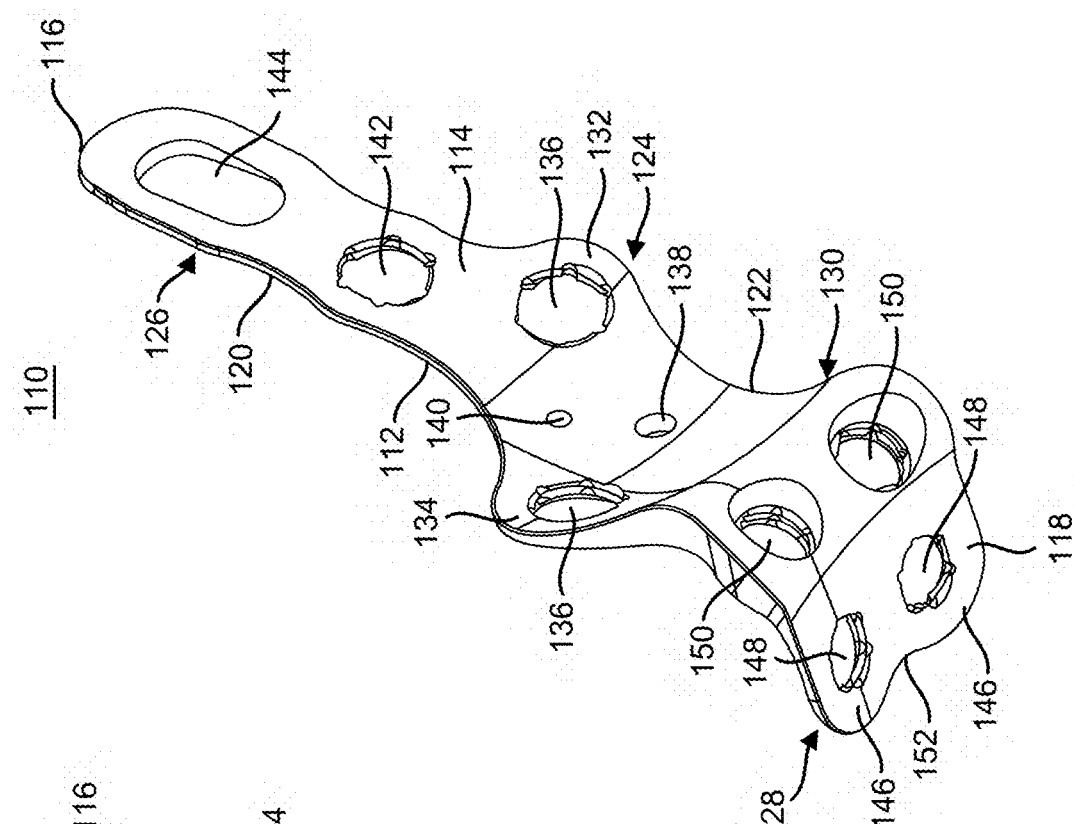
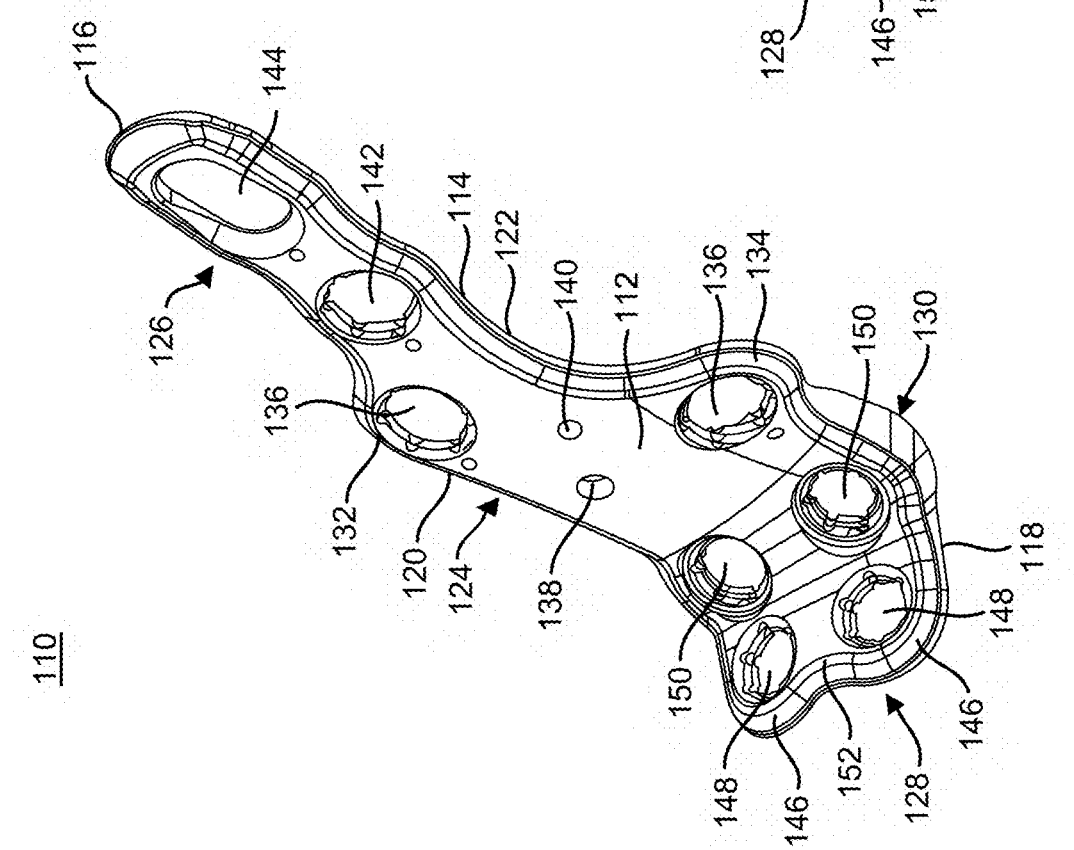

IMPLANTS, ALIGNMENT GUIDES, SYSTEMS AND METHODS OF USE

CROSS-REFERENCE TO RELATED APPLICATIONS

This application is a continuation of PCT Application No. PCT/US2019/041305 filed on Jul. 11, 2019, entitled Implants, Alignment Guides, Systems and Methods of Use, which claims benefit to U.S. provisional application No. 62/696,788 filed Jul. 11, 2018, entitled Implant, Alignment Guide, System and Methods of Use, and U.S. provisional application No. 62/811,980 filed Feb. 28, 2019, entitled Implants, Alignment Guides, Systems and Methods of Use, which are incorporated herein by reference in their entireties.

FIELD OF INVENTION

The present disclosure relates generally to general surgery and orthopaedic implants used for achieving bone fusion. More specifically, but not exclusively, the present disclosure relates to surgical devices, implants, guides, and systems for fixation of human bones, such as, the foot and ankle bones, and to stabilize the realignment of a fracture, dislocation, fusion or the like of the bones of the foot and ankle.

BACKGROUND OF THE INVENTION

Currently available guides and systems for foot and ankle fusion surgeries include fixed trajectories for insertion of fasteners to fuse the patient's bones. The currently available guides and systems limit a surgeon's options and do not allow for adjustment based on each patient's unique anatomy.

Accordingly, it is an object of the present disclosure to overcome one or more of the above-described drawbacks and/or disadvantages of the currently used procedures. For example, in view of the deficiencies of the currently available implants, guides, systems and methods it would be desirable to develop implants, guides, systems and methods that allow for adjustment of the fastener insertion trajectories to overcome the above-noted drawbacks of the currently available systems and surgical solutions.

SUMMARY OF THE INVENTION

Aspects of the present disclosure provide bone fixation devices for use in a method of fusing bones. Specifically, the present disclosure relates to surgical devices, implants, guides, systems and methods for fixation of human bones, such as, the foot and ankle bones, and to stabilize realignment of a fracture, dislocation, fusion or the like of the foot or ankle bones.

In one aspect, provided herein is a fusion system, including an alignment guide and an implant, wherein the alignment guide couples to the implant.

In another aspect, provided herein is an alignment guide, including a body, a fixation member engaging a first end of the body, and a tissue protector engaging a second end of the body.

In yet another aspect, provided herein is an implant, including a body portion, an extension portion extending away from a first end of the body portion, a curved portion extending away from a second end of the body portion, and a foot member extending away from the curved portion perpendicular to the body portion.

In a further aspect, provided herein is a method for using a fusion system, including preparing at least one joint and inserting fixation wires across the at least one joint. The method may also include obtaining a plate and placing the plate over a first bone and second bone of the at least one joint. The method further includes coupling the plate to the first bone and the second bone and obtaining an alignment guide. In addition, the method includes coupling the alignment guide to the plate and rotating the alignment guide to a desired angle of insertion for a compression fastener. The method also includes securing the alignment guide at the desired angle of insertion and inserting a k-wire through the alignment guide and across the at least one joint. The method further includes removing the alignment guide from the plate and inserting the compression fastener through the first bone and second bone. Finally, the method includes removing the k-wire and closing an incision.

These, and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. The drawings are only for purposes of illustrating preferred embodiments and are not to be construed as limiting the disclosure. It is emphasized that, in accordance with the standard practice in the industry, various features are not drawn to scale. In fact, the dimensions of the various features may be arbitrarily increased or reduced for clarity of discussion. The foregoing and other objects, features and advantages of the disclosure are apparent from the following detailed description taken in conjunction with the accompanying drawings in which:

FIG. 3 is a top perspective view of a plate of the fusion system of FIG. 1, in accordance with an aspect of the present disclosure;

FIG. 4 is a bottom perspective view of the plate of FIG. 3, in accordance with an aspect of the present disclosure;

DETAILED DESCRIPTION OF THE INVENTION

Figure 1:
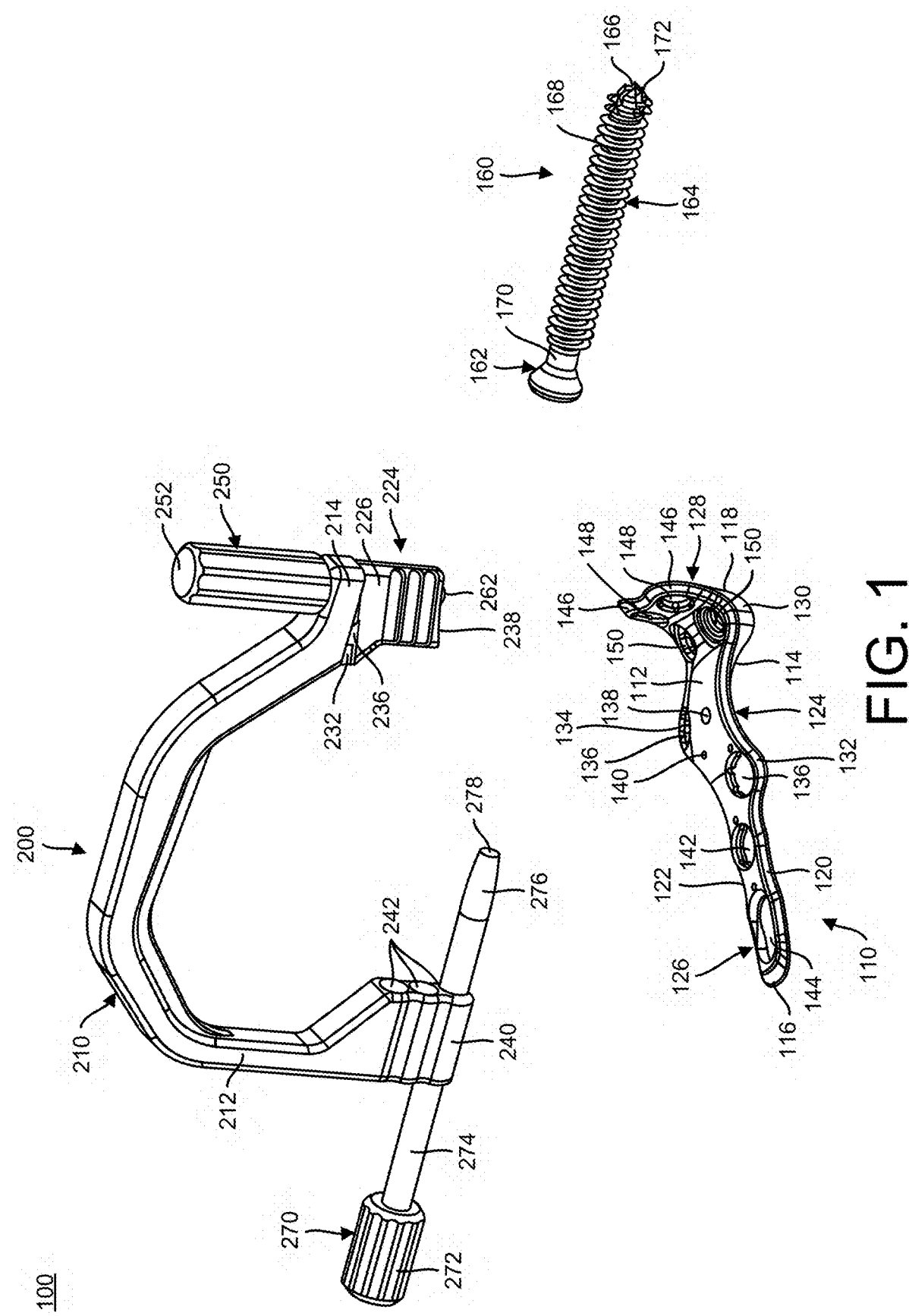
FIG. 1 is a first perspective view of a fusion system, in accordance with an aspect of the present disclosure.

Generally stated, disclosed herein are embodiments of devices, implants, guides, and systems for fixation of human bones, such as, foot and ankle bones. Further, surgical methods for using the devices, implants, guides, and systems for fixation of human bones to stabilize realignment of a fracture, dislocation, fusion or the like of the foot and ankle bones are discussed.

In this detailed description and the following claims, the words proximal, distal, anterior or plantar, posterior or dorsal, medial, lateral, superior and inferior are defined by their standard usage for indicating a particular part of a bone, implant, device or guide according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices and methods are described herein with reference to use with the bones of the foot and ankle, the bones of the foot, ankle and lower leg may be used to describe the surfaces, positions, directions or orientations of the devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices and methods, and the aspects, components, features and the like thereof, described herein with respect to the right foot and ankle may be mirrored so that they likewise function with the left foot and ankle. Further, the devices and methods, and the aspects, components, features and the like thereof, disclosed herein are described with respect to the foot and ankle for brevity purposes, but it should be understood that the devices and methods may be used with other bones of the body having similar structures, for example the upper extremity, and more specifically, with the bones of the wrist, hand, and arm.

Figure 2:
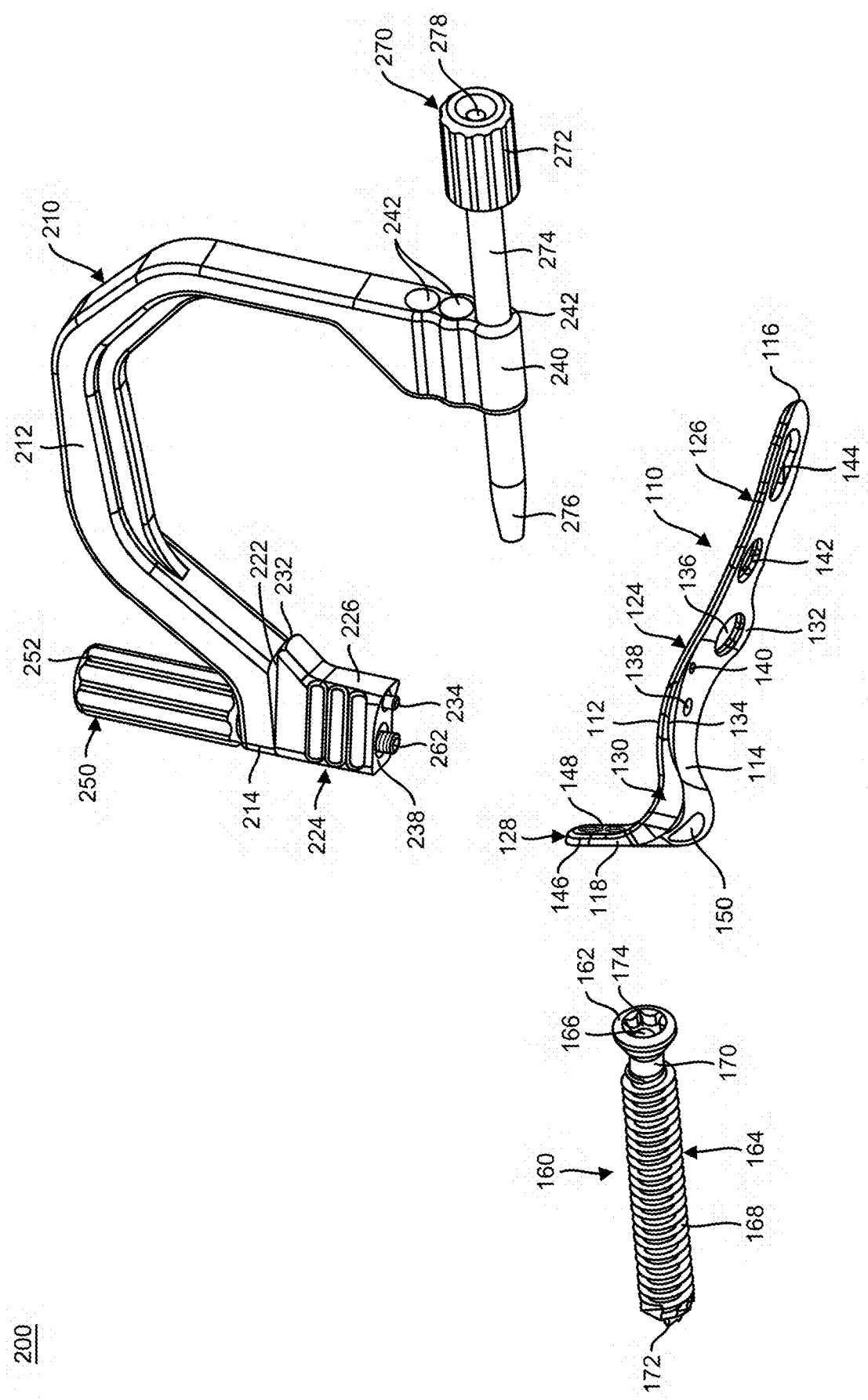
FIG. 2 is a second perspective view of the fusion system of FIG. 1, in accordance with an aspect of the present disclosure.

Referring to the drawings, wherein like reference numerals are used to indicate like or analogous components throughout the several views, and with particular reference to FIGS. 1 and 2, there is illustrated a fusion system or ankle fusion plate system 100. The fusion system 100 may include an implant, plate or bone plate 110, an alignment guide 200, and a fastener 160. The alignment guide 200 may be coupled to the plate 110 for insertion of the fastener 160 across a joint without contacting the fasteners or screws (not shown) inserted through the plate 110. Each component of the fusion system 100 may be made from, for example, a biocompatible material, including but not limited to a metal, polymer, composite, etc.

Figure 10:
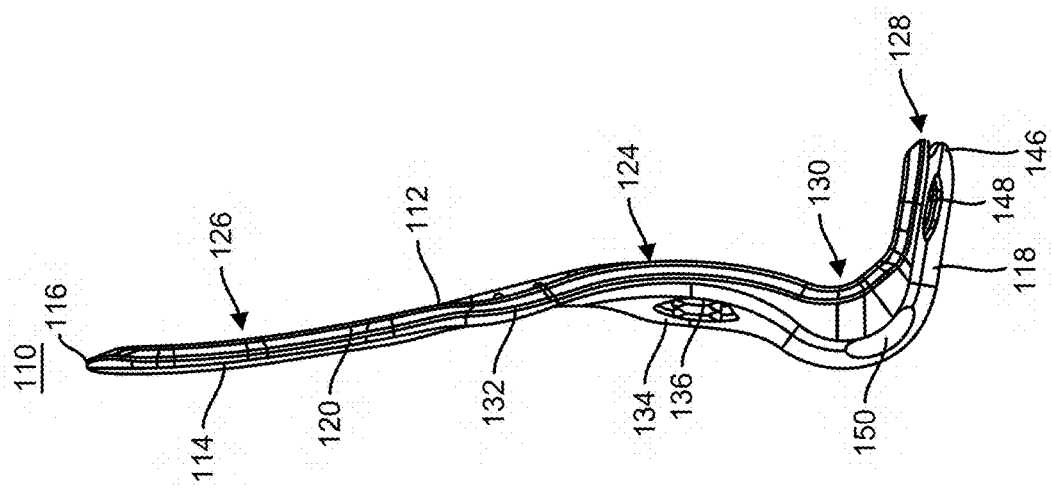
FIG. 10 is a second side view of the plate of FIG. 3, in accordance with an aspect of the present disclosure.
Figure 9:
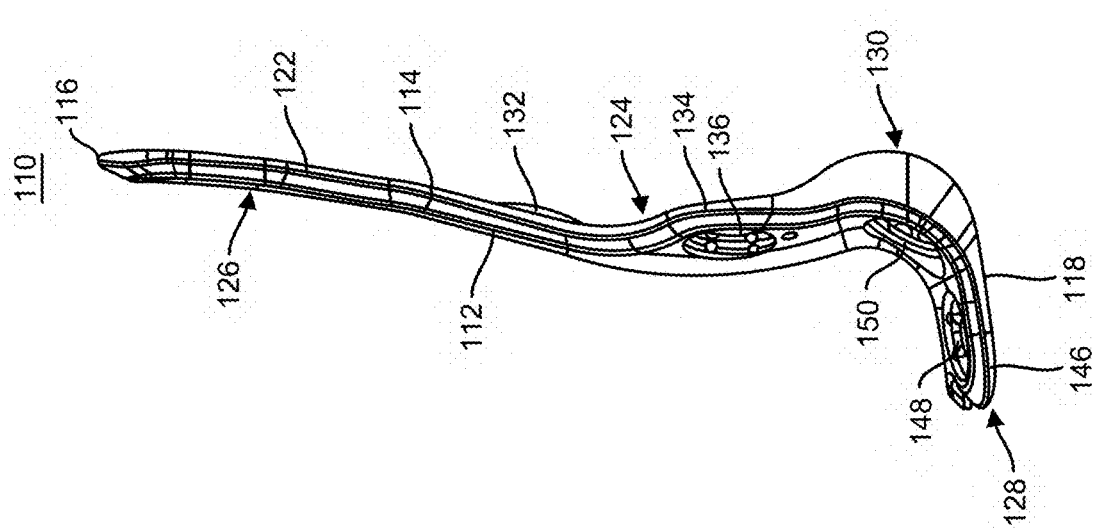
FIG. 9 is a first side view of the plate of FIG. 3, in accordance with an aspect of the present disclosure.
Figure 11:
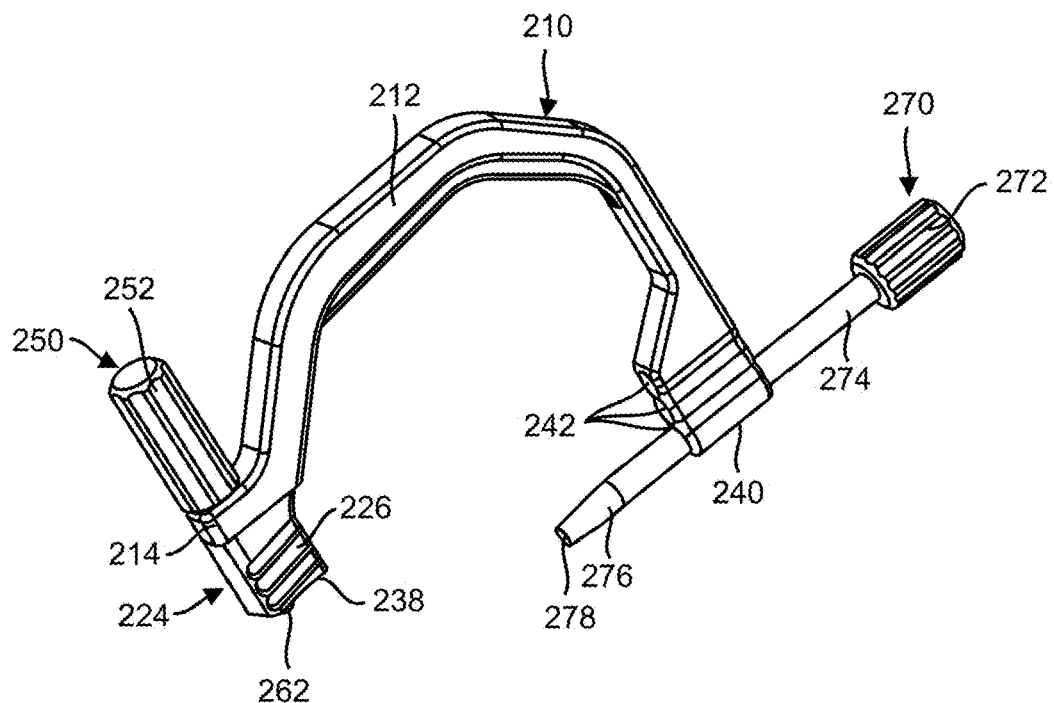
FIG. 11 is a perspective view of an alignment guide of the fusion system of FIG. 1, in accordance with an aspect of the present disclosure.
Figure 12:
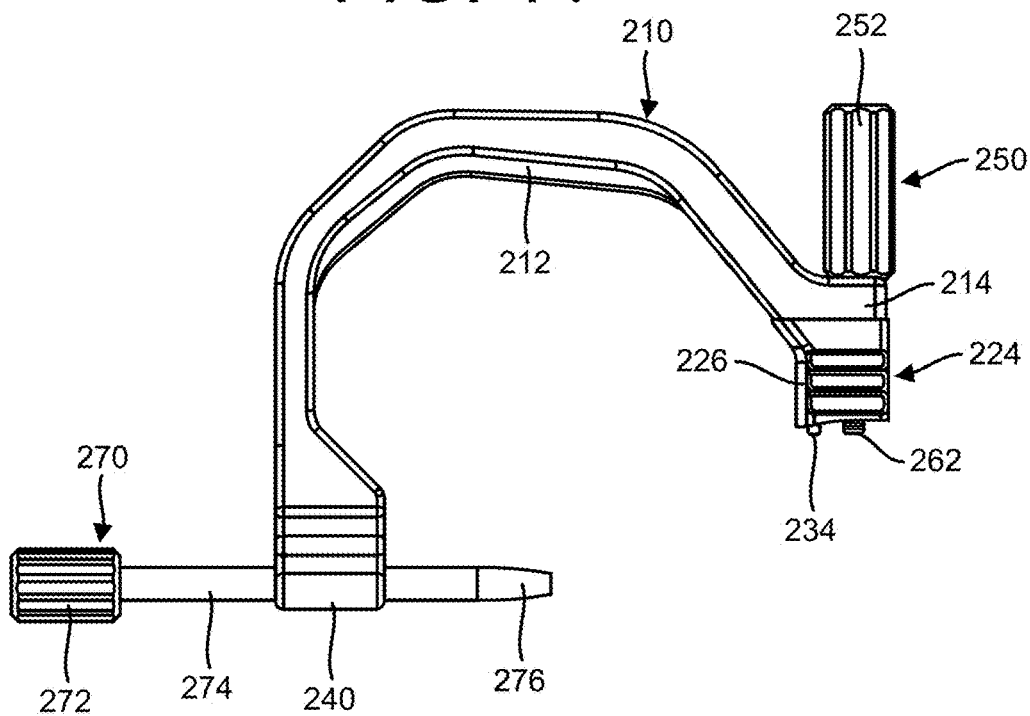
FIG. 12 is a side view of the alignment guide of FIG. 11, in accordance with an aspect of the present disclosure.
Figure 13:
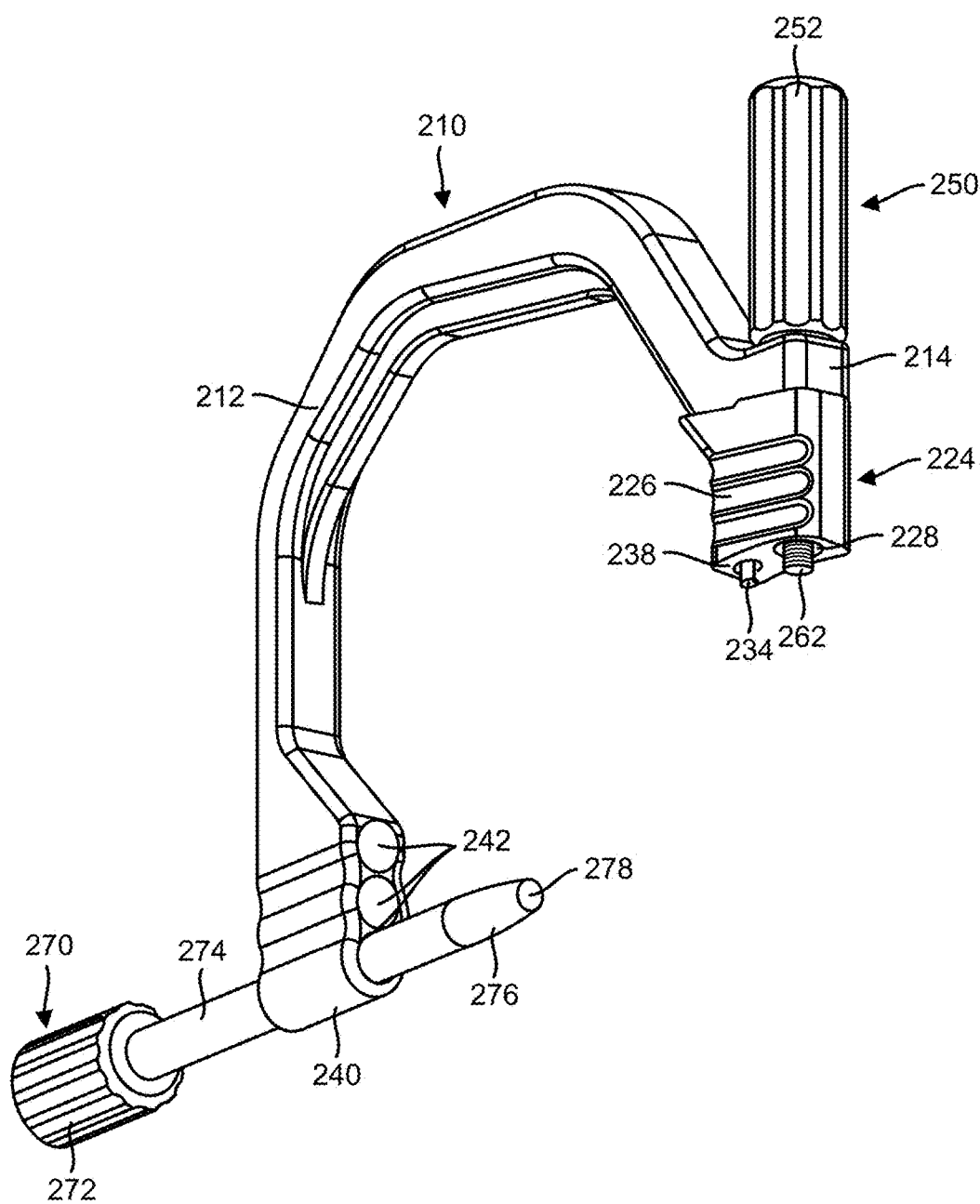
FIG. 13 is a first end perspective view of the alignment guide of FIG. 11, in accordance with an aspect of the present disclosure.
Figure 14:
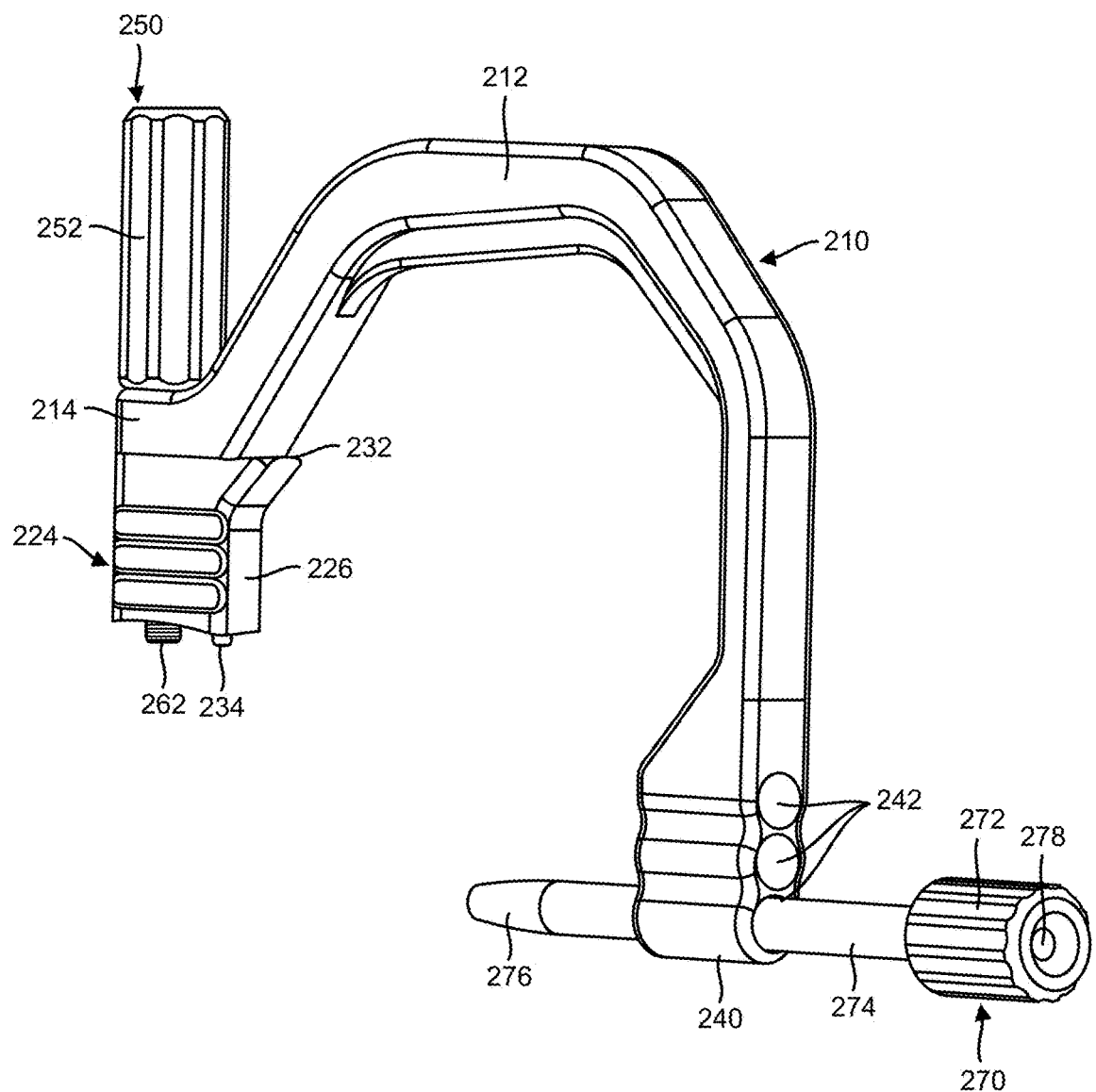
FIG. 14 is a second end perspective view of the alignment guide of FIG. 11, in accordance with an aspect of the present disclosure.
Figure 15:
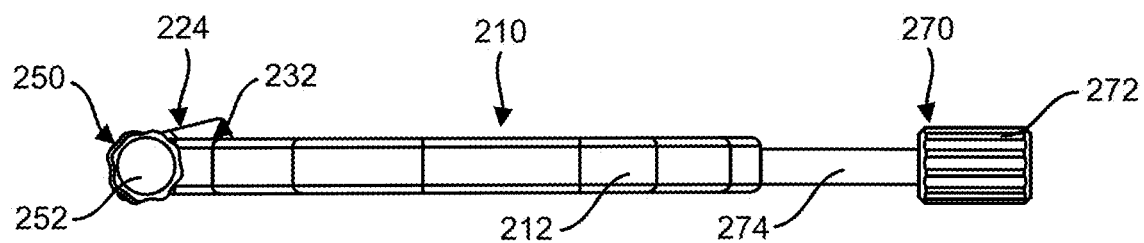
FIG. 15 is a top view of the alignment guide of FIG. 11, in accordance with an aspect of the present disclosure.
Figure 16:
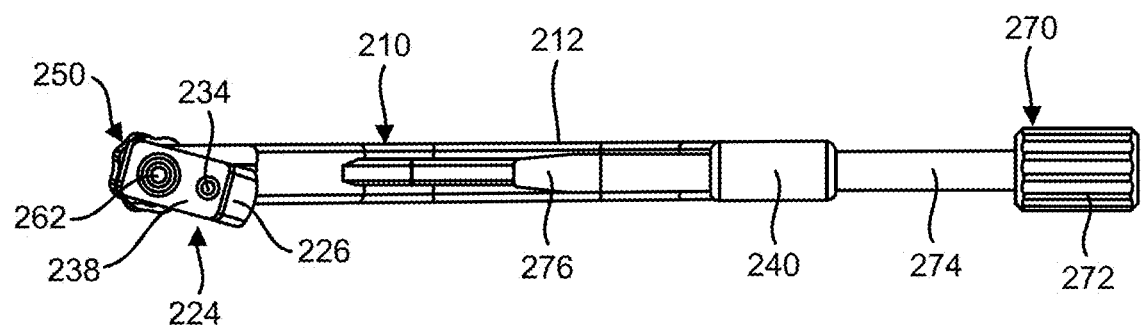
FIG. 16 is a bottom view of the alignment guide of FIG. 11, in accordance with an aspect of the present disclosure.
Figure 17:
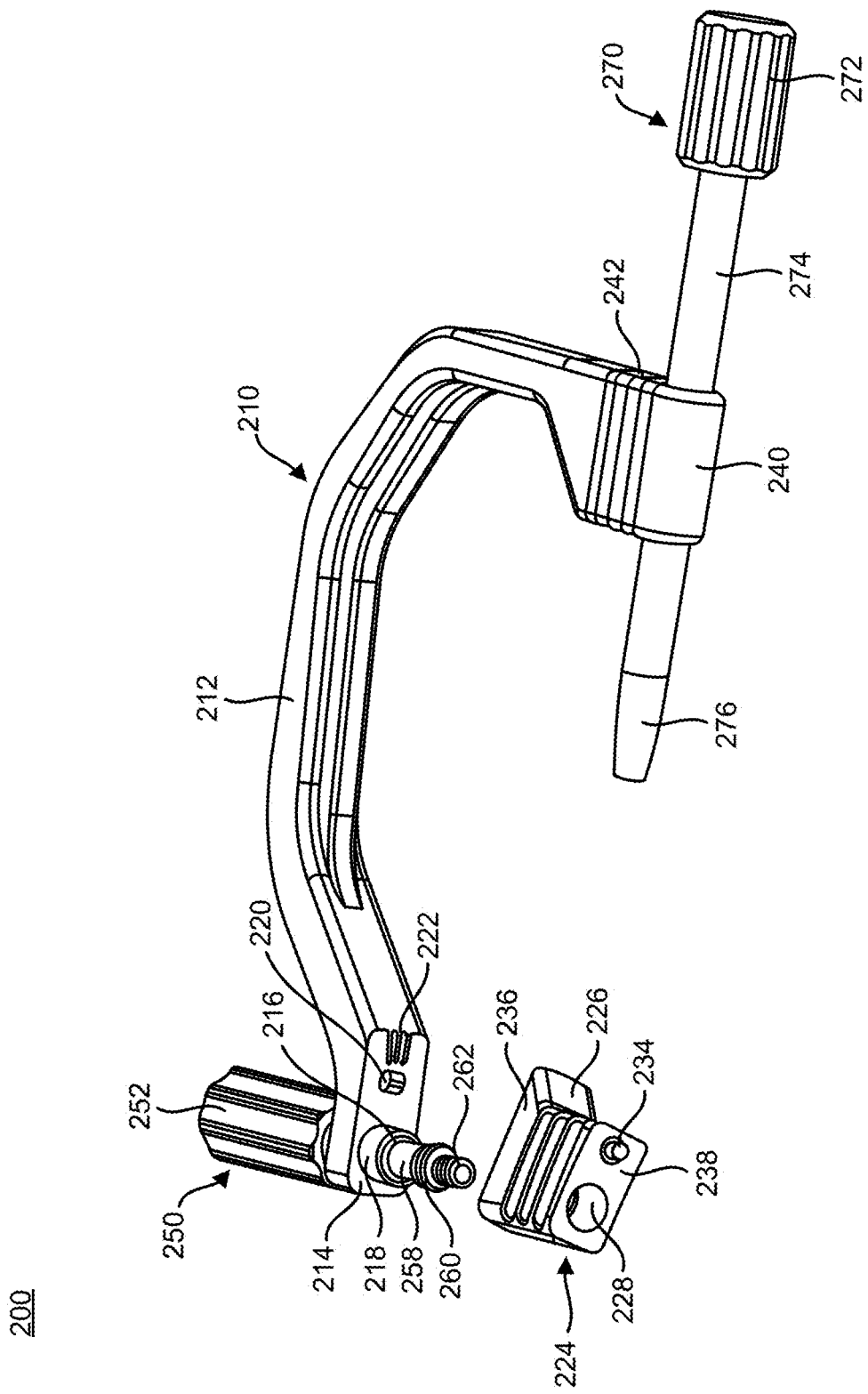
FIG. 17 is a partially exploded, bottom perspective view of the alignment guide of FIG. 11, in accordance with an aspect of the present disclosure.
Figure 18:
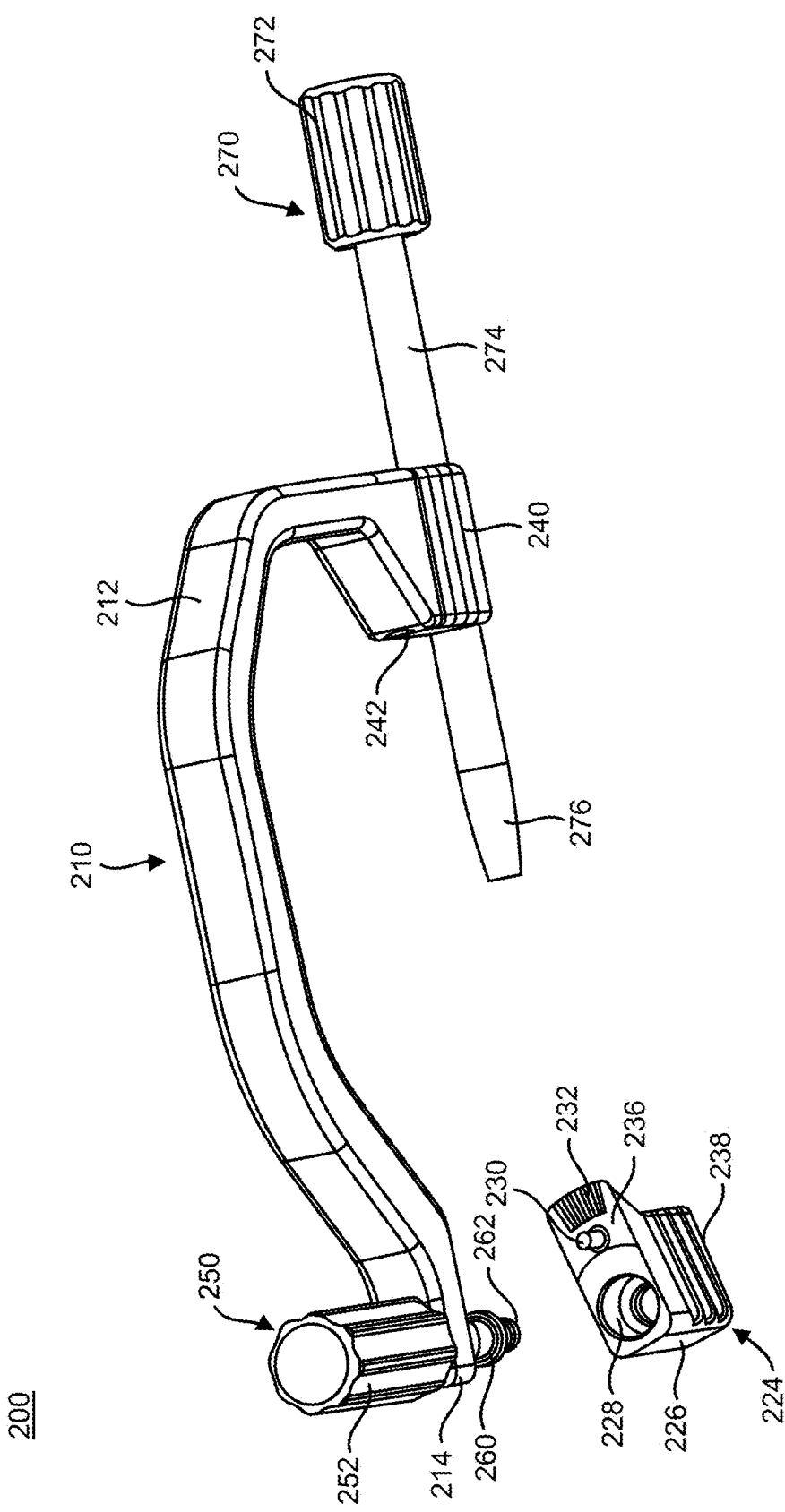
FIG. 18 is a partially exploded, top perspective view of the alignment guide of FIG. 11, in accordance with an aspect of the present disclosure.

Referring now to FIGS. 3-10, the implant or plate 110 is shown. The plate 110 includes a top surface 112 opposite a bottom surface 114, a first end 116 opposite a second end 118, and a first side 120 generally opposite a second side 122. The plate 110 also includes a body portion or intermediate portion 124, an extension portion or proximal portion 126 extending from the proximal end of the body portion 124 to the first end 116, and a foot member or distal portion 128 extending from the distal end of the body portion 124 at the second end 118. At least a portion of the foot member 128 may extend away from the body portion 124, for example, generally perpendicular to the top surface 112 of the body portion 124. The plate 110 may further include a transition portion or connecting portion 130 positioned between the body portion 124 and the foot member 128. The transition portion 130 may be, for example, a curved portion positioning the body portion 124 generally perpendicular to the foot member 128, as shown in FIGS. 9 and 10. The foot member 128 may be angled with respect to the body portion 124 and in an embodiment the angle may, for example, range from approximately 80° to 120°, and more specifically may be approximately 100°.

Figure 6:
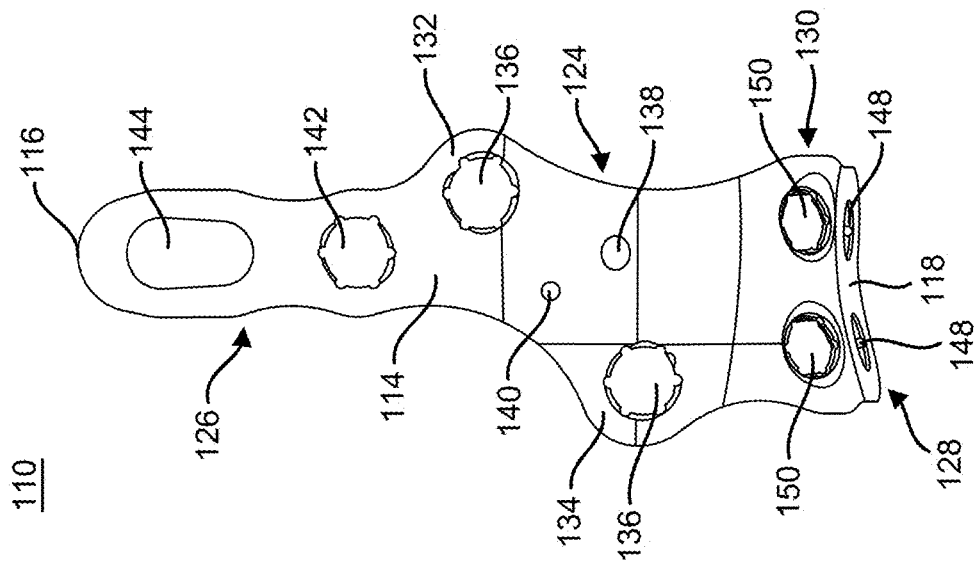
FIG. 6 is a bottom view of the plate of FIG. 3, in accordance with an aspect of the present disclosure.
Figure 5:
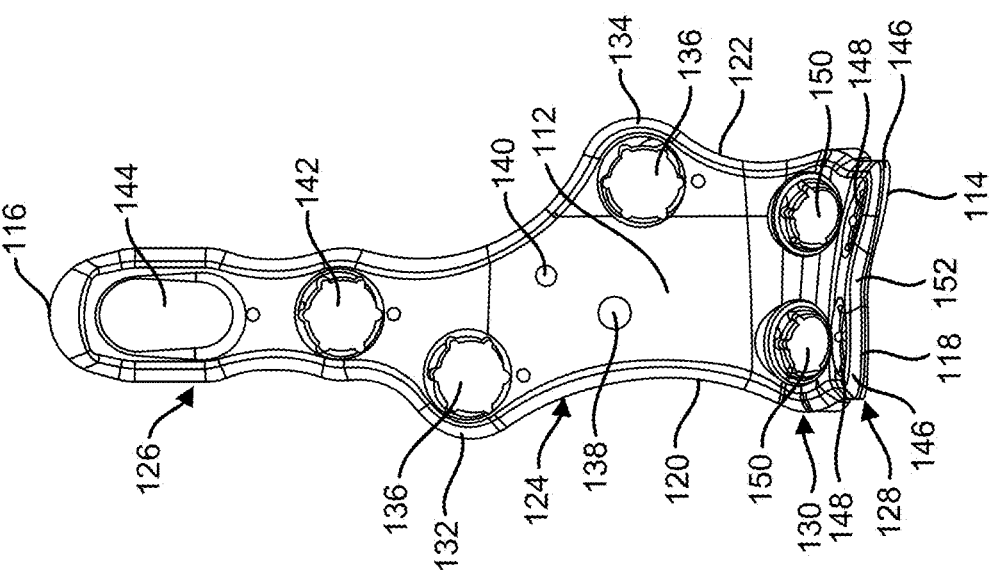
FIG. 5 is a top view of the plate of FIG. 3, in accordance with an aspect of the present disclosure.
Figure 7:
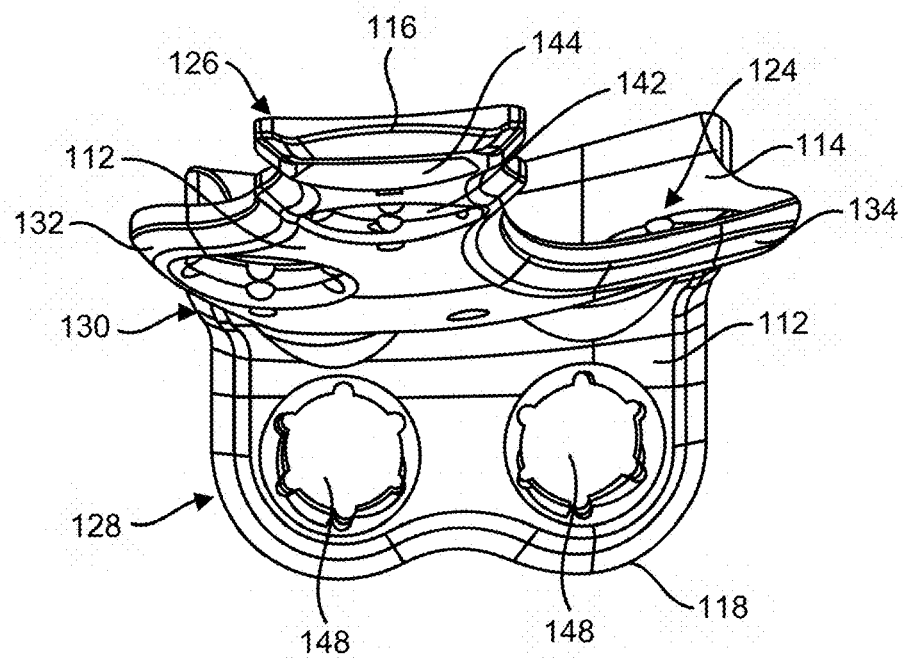
FIG. 7 is a first end view of the plate of FIG. 3, in accordance with an aspect of the present disclosure.
Figure 8:
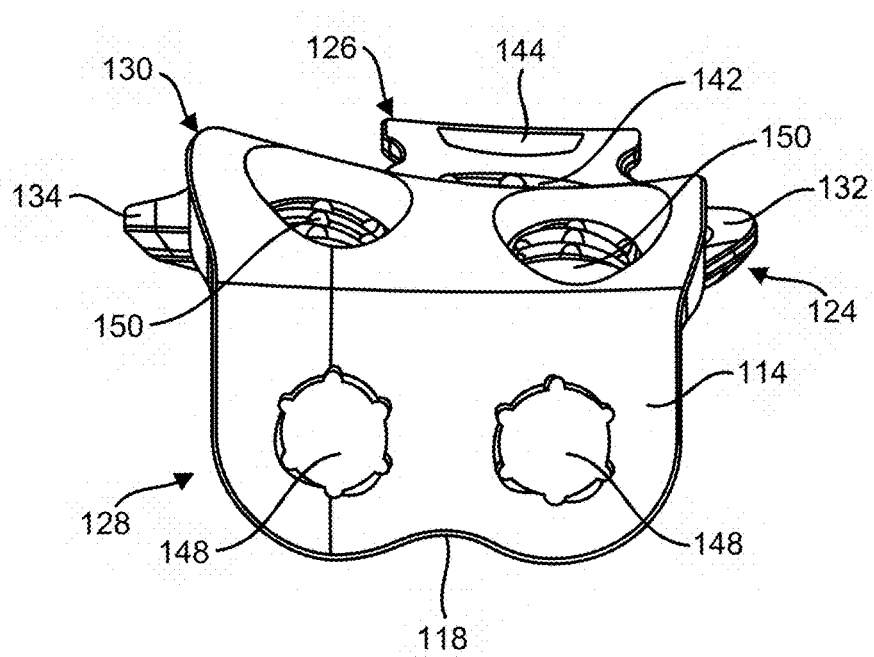
FIG. 8 is a second end view of the plate of FIG. 3, in accordance with an aspect of the present disclosure.

With continued reference to FIGS. 3-10 and more specifically FIGS. 5 and 6, the body portion 124 may include at least one lobe 132, 134, for example, a first lobe 132 and a second lobe 134. The first lobe 132 may, for example, extend at least partially away from the first side 120 of the plate 110. The second lobe 134 may, for example, extend at least partially away from the second side 122 of the plate 110. Each lobe 132, 134 may include a first through hole or fastener hole 136 extending through the plate 110 from a top surface 112 to a bottom surface 114. The first through hole 136 extending through the first lobe 132 may be positioned, for example, lateral to a midline of the plate 110. The first through hole 136 extending through the second lobe 134 may be positioned, for example, medial to the midline of the plate 110. The first through holes 136 may be, for example, positioned in the body portion 124 to allow for the fastener 160 to pass between screws inserted into through holes 136 without contacting the screws. The body portion 124 may also include a first opening or engagement opening 138 and a second opening or alignment opening 140 for coupling to the alignment guide 200. The first opening 138 may be, for example, offset from the second opening 140 along a longitudinal axis of the plate 110. The first opening 138 may also be positioned near the first side 120 of the plate 110 and between the first side 120 and the second opening 140. The second opening 140 may be positioned near the second side 122 of the plate 110 and between the second side 122 and the first opening 138. A line connecting the first opening 138 and second opening 140 may form an angle with respect to a midline of the plate 110 and the angle may be, for example, approximately 24° to 34° and more specifically approximately 29°. This angle also defines the angle between the midline of the plate 110 and the longitudinal axis of the arm 212 of the alignment guide 210, as described in greater detail below. The body portion 124 of the plate may also be, for example, angled between the extension portion 126 or proximal end and the second lobe 134 on the second side 122 of the plate 110. The angled portion of the second side 122 may also be, for example, curved along the angle, as shown in FIGS. 5 and 6. In addition, the second side 122 may be, for example, curved between the second lobe 134 and the transition portion 130. Further, the first side 120 may be, for example, curved between the first lobe 132 and the transition portion 130. Also, as shown in FIGS. 9 and 10, the body portion 124 may be, for example, curved as the body portion 124 extends between the extension portion 126 and the transition portion 130.

As shown in FIGS. 3-6, the extension portion 126 of the plate 110 may include at least one second through hole or fastener hole 142 positioned along the extension portion 126. The extension portion 126 may also include a slot, compression slot, or opening 144. The slot 144 may be positioned, for example, at or near the first end 116 of the plate 110. The slot 144 may be, for example, longer than the through holes 136, 142. The at least one second through hole 142 may be positioned, for example, between the slot 144 and the body portion 124. The at least one second through hole 142 and the slot 144 may be, for example, positioned along the midline of the plate 110. The extension portion 126 may have, for example, a width that is smaller than the width of the body portion 124 and the foot member 128.

Referring now to FIGS. 3, 4, 7 and 8, the foot member 128 may include at least one third lobe or distal lobe 146. As depicted, the foot member 128 includes two distal lobes 146. Each lobe 146 includes a third through hole or fastener hole 148 for receiving a fastener or bone screw to secure the plate to a patient's foot. The through holes 148 may extend through the plate 110 perpendicular to the direction that the through holes 136, 142 extend through the plate 110. The through hole 148 positioned near the first side 120 of the plate 110 may be, for example, positioned along the midline of the plate 110, while the through hole 148 positioned near the second side 122 of the plate 110 may be, for example, positioned medial to the midline. The foot member 128 may also include, for example, a ramped portion 152 positioned between the two lobes 146 to allow for surrounding tissue to slide over the distal end 118 of the plate 110 without irritating the tissue. The connecting portion 130 may also include at least one fourth through hole or fastener hole 150 extending through the plate 110, as shown in FIGS. 3, 4, 7, and 8. As shown, the connecting portion 130 may include, for example, two through holes 150. The through holes 150 may, for example, extend through the curved section of the connecting portion 130 positioning the through holes 150 at an angle relative to both the through holes 136, 142 and the through holes 148. The through hole 150 positioned near the first side 120 of the plate 110 may be, for example, positioned along the midline of the plate 110, while the through hole 150 positioned near the second side 122 of the plate 110 may be, for example, positioned medial to the midline Referring now to FIGS. 1 and 2, the fastener 160 may be, for example, a compression screw, compression fastener, beam fastener, bone screw, beam screw, fixator, elongate member, rod, lag screw, headless screw, a solid screw, or screw for crossing a joint or fracture. The fastener or screw 160 may include a head portion 162 and a shaft or shank portion 164 extending away from a bottom surface of the head portion 162. The fastener 160 may also include a cannulation or through hole 166 extending from a first end through the head portion 162 and the shaft portion 164 to the second end. The cannulation 166 may be, for example, sized and shaped to receive a temporary fixation or guiding member, such as, a k-wire, guide wire, olive wire, pin, or the like, as known by one of ordinary skill in the art, as described in greater detail below with reference to FIGS. 32 and 33. As shown in FIG. 2, the head portion 162 may include, for example, a drive feature 174 for receiving a drill or screw driver to insert the fastener 160 into a patient's bones. The shaft portion 164 of the fastener 160 may include, for example, a threaded portion 168 and a smooth portion 170 along the length of the shaft portion 164. The length of the threaded portion 168 and smooth portion 170 may, for example, vary depending on the bones the fastener 160 will be inserted into, in the depicted embodiment the threaded portion 168 is longer than the smooth portion 170. The shaft portion 164 may also include at least one tooth 172 positioned at the end of the shaft portion 164 to assist with insertion of the fastener 160 into a patient's bones.

Referring now to FIGS. 11-22, the alignment guide or bone plate alignment guide 200 is shown. The alignment guide 200 may include a body 210, a fixation member or coupling member 250, and a guide pin tissue protector 270. The fixation member 250 may be received in a first end of the body 210 and the guide pin tissue protector 270 may be received in a second end of the body 210. The alignment guide 200 may also include at least one guide wire or pin (not shown) for insertion through the guide pin tissue protector 270.

Figure 19:
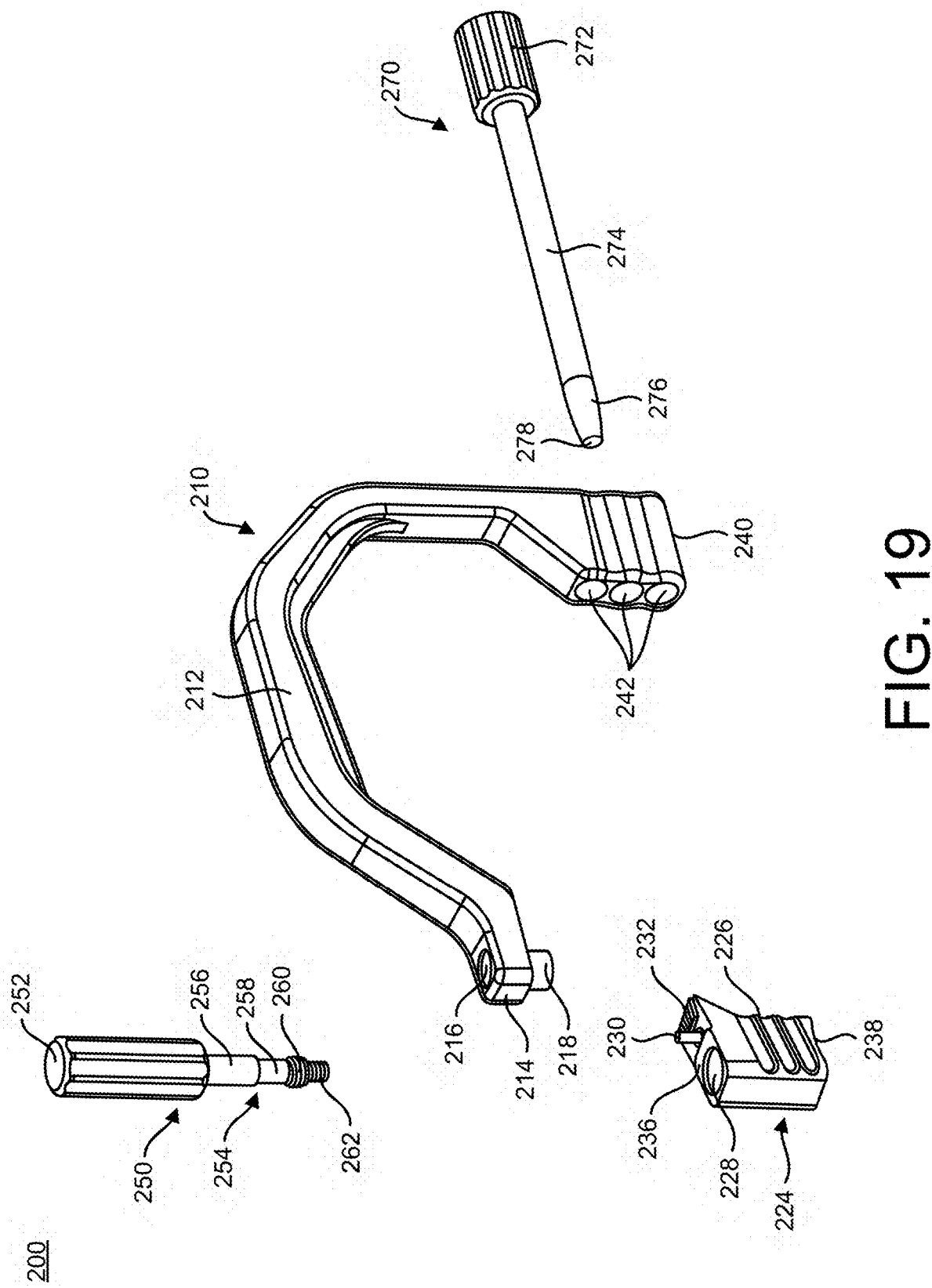
FIG. 19 is an exploded, first perspective view of the alignment guide of FIG. 11, in accordance with an aspect of the present disclosure.
Figure 20:
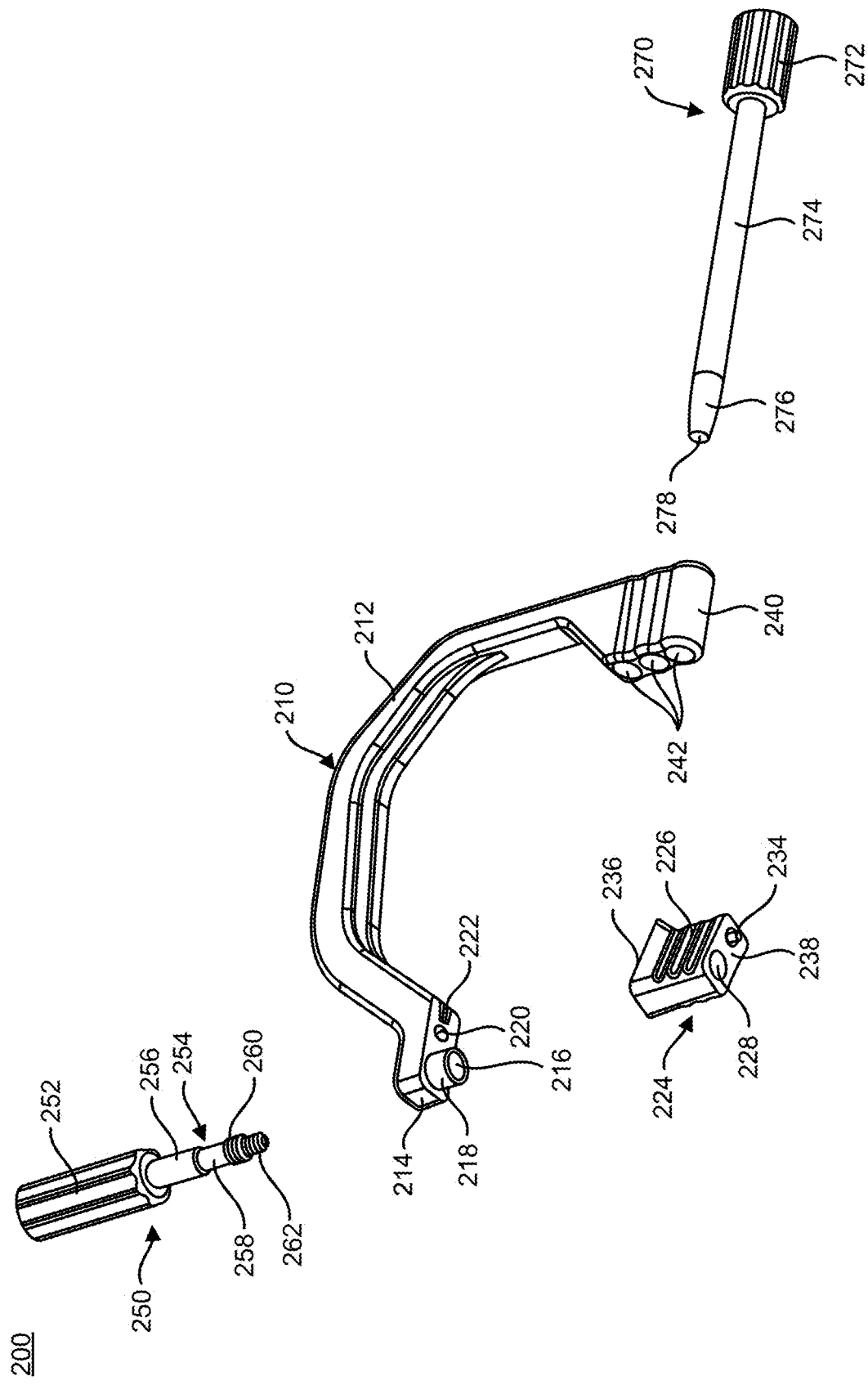
FIG. 20 is an exploded, second perspective view of the alignment guide of FIG. 11, in accordance with an aspect of the present disclosure.
Figure 21:
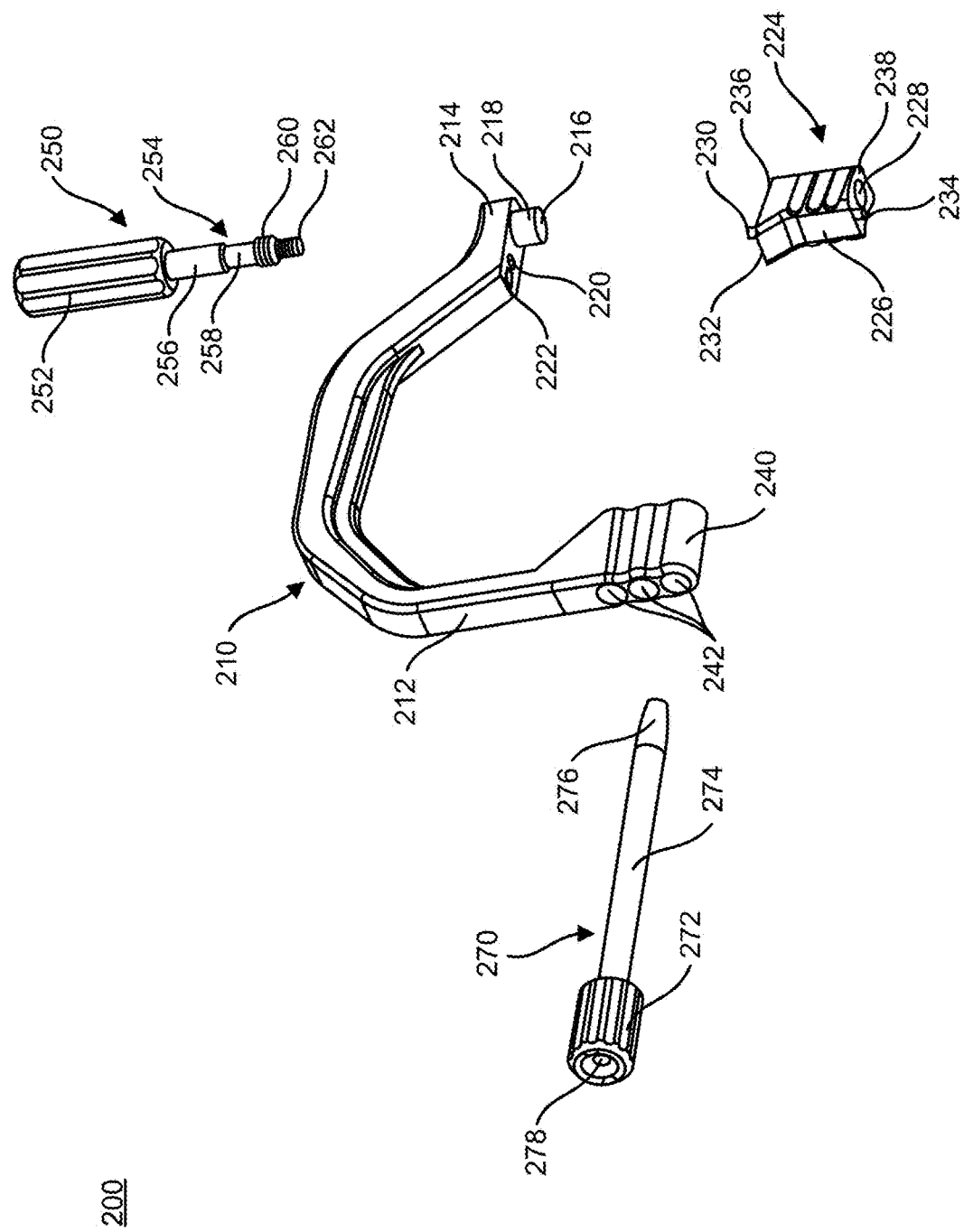
FIG. 21 is an exploded, third perspective view of the alignment guide of FIG. 11, in accordance with an aspect of the present disclosure.

As shown in FIGS. 19-22, the body 210 may include an arm 212 with an attachment portion 214 at the first end of the body 210 and an alignment portion 240 at the second end of the body 210. The attachment portion 214 may include a through hole 216 extending through the arm 212 near the first end. The through hole 216 may also extend through a coupling protrusion or engagement protrusion 218 extending away from a bottom surface of the attachment portion 214. The attachment portion 214 may also include an opening or stop opening 220 extending into the attachment portion 214 of the arm 212 from the bottom surface, as shown in FIGS. 20 and 21. The opening 220 may be positioned adjacent to the engagement protrusion 218. With continued reference to FIGS. 20 and 21, the attachment portion 214 also includes a first engagement surface 222 with, for example, alternating protrusions and recesses. The protrusions of the first engagement surface 222 may be, for example, spaced apart to form recesses between the protrusions. The protrusions of the first engagement surface 222 may be, for example, male teeth. The protrusions of the first engagement surface 222 may also be, for example, positioned with the interior ends of the protrusions positioned closer together than the exterior ends of the protrusions to form a curved or arced shape. Each protrusion of the first engagement surface 222 may be spaced apart, for example, to allow for approximately 2.5° of rotation from a central axis of the arm 212. In one embodiment, the protrusions allow for, for example, a maximum of approximately 5° of rotation in each direction from the central axis to provide a total of approximately 10° of rotation. The first engagement surface 222 may be, for example, positioned adjacent to the opening 220 on a side of the bottom surface of the attachment portion 214 and opposite the through hole 218.

Figure 22:
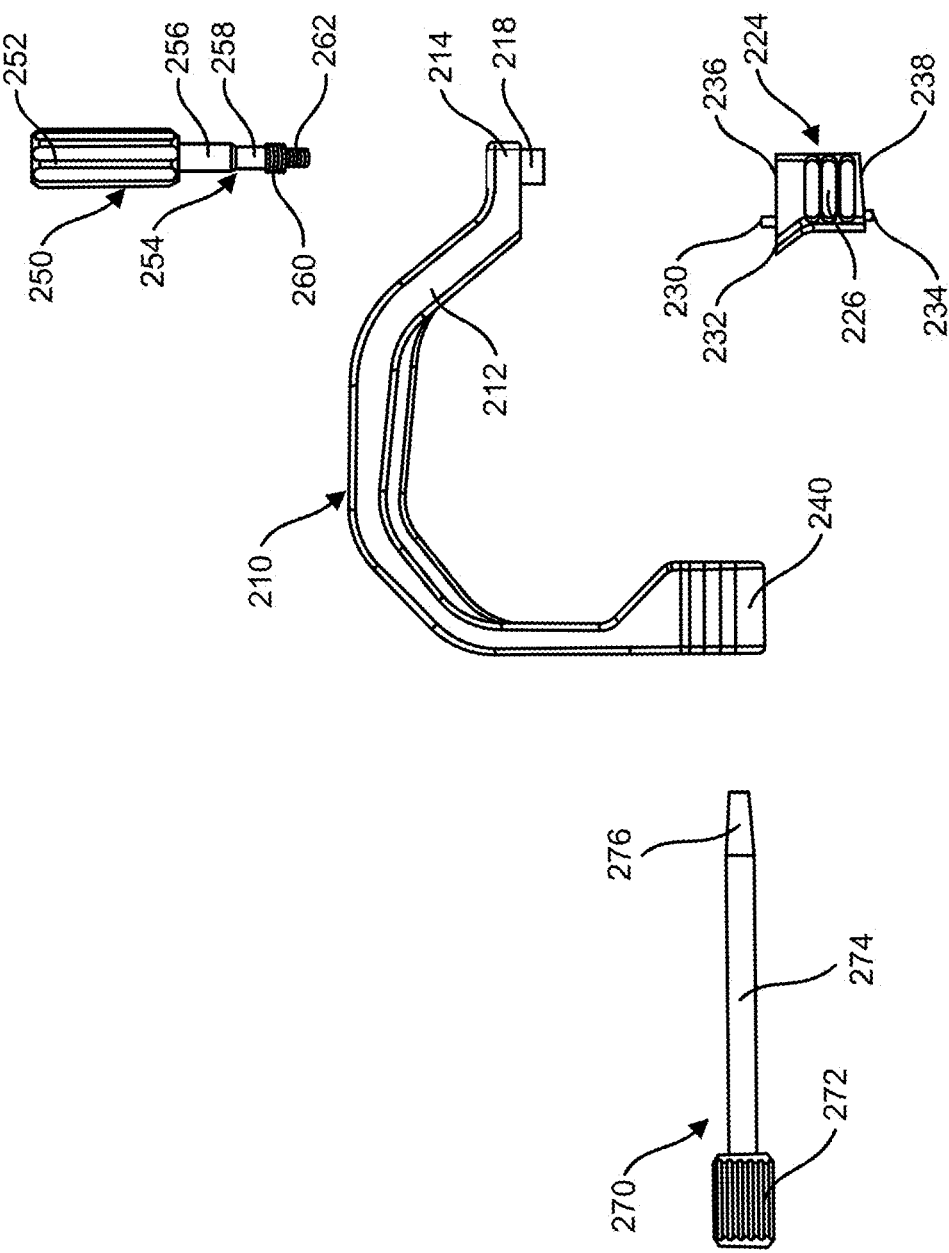
FIG. 22 is an exploded, side view of the alignment guide of FIG. 11, in accordance with an aspect of the present disclosure.

With continued reference to FIGS. 19-22, the alignment guide 200 may also include a rotation member 224. The rotation member 224 may engage the bottom surface of the attachment portion 214 of the body 210. The rotation member 224 may include a body 226 with a through hole 228 extending through the body 226 from a top surface 236 to a bottom surface 238. The through hole 228 may be, for example, sized and shaped to receive the engagement protrusion 218. The rotation member 224 may also include a stop peg, stop pin or stop protrusion 230 extending away from the top surface 236 of the body 226, as shown in FIGS. 19, 21 and 22. The stop pin 230 may be, for example, sized and shaped to be inserted into the opening 220 on the bottom surface of the attachment portion 214. The shapes of the opening 220 and stop pin 230 prevent the alignment guide 210 from being over-rotated with respect to the plate 110. For example, the opening 220 and stop pin 230 may allow for approximately 10° of rotation relative to a center line drawn between the first opening 138 and the second opening 140 on the plate 110. The top surface 236 of the body 226 of the rotation member 224 may also include a second engagement surface 232 with, for example, alternating protrusions and recesses. The protrusions of the second engagement surface 232 may be, for example, spaced apart to form recesses between the protrusions. The recesses of the second engagement surface 232 may be, for example, female teeth. The protrusions of the second engagement surface 232 may also be, for example, positioned with the interior ends of the protrusions positioned closer together than the exterior ends of the protrusions to form a curved or arced shape. Each recess of the second engagement surface 232 may be spaced apart, for example, to allow for approximately 2.5° of rotation from a central axis of the arm 212. In one embodiment, the recesses allow for, for example, a maximum of approximately 5° of rotation in each direction from the central axis to provide a total of approximately 10° of rotation. The rotation member 224 may further include a second peg or alignment pin 234 extending away from the bottom surface 238 of the body 226, as shown in FIGS. 20-22. The second alignment pin 234 may be positioned adjacent to the through hole 228. The second alignment pin 234 may be, for example, sized and shaped to engage the alignment opening 140 of the plate 110. The bottom surface 238 of the rotation member 224 may be, for example, curved, arced, or otherwise shaped to match the shape of a top surface of the plate 110 where the rotation member 224 engages the plate 110.

The alignment portion 240 may include at least one hole 242, as shown in FIGS. 1, 2, 13, 14, and 19-21. The alignment portion 240 may include, for example, three holes 242, as shown in the depicted embodiment. The three holes 242 may be positioned linearly as the alignment portion 240 extends away from the arm 212. The holes 242 may be, for example, straight or angled to a desired insertion position as the holes 242 extend through the arm 212 of the body 210. In the depicted embodiment, the holes 242 extend through the alignment portion 240 parallel to each other. The holes 242 may be, for example, sized and shaped to receive the guide pin tissue protector 270.

As shown in FIGS. 1, 2 and 19-22, the fixation member 250 may include a knob 252 and a shaft 254 extending away from a bottom surface of the knob 252. The shaft 254 may include a first portion 256 extending away from the knob 252 and a second portion 258 extending away from the first portion 256. The first portion 256 may have, for example, a diameter larger than the diameter of the second portion 258. The shaft 254 may also include at least one engagement member 260, 262 for coupling to the engagement opening 138 of the plate 110. The at least one engagement member 260, 262 may include a first engagement member 260 and a second engagement member 262. The first engagement member 260 may be, for example, positioned at an end of the second portion 258 opposite the first portion 256. The second engagement member 262 may extend away from the first engagement member 260 on a side opposite the second portion 258. The first engagement member 260 may have, for example, a first diameter and the second engagement member 262 may have, for example, a second diameter. The first diameter may be, for example, larger than the second diameter. The first and second engagement members 260, 262 may be, for example, threaded to engage corresponding threads in the opening 138 of the plate 110 as shown in the depicted embodiment, deformable to be removeably press fit into the opening 138 in the plate 110, or another similar configuration that achieves a coupling of the alignment guide 200 to the plate 110.

As shown in FIGS. 1, 2, 11-14, and 16-22, the guide pin tissue protector 270 may include a handle portion 272 and a shaft portion 274 extending away from the handle portion 272. The handle portion 272 may be coupled to the first end of the shaft portion 274 and a tip 276 may be positioned at the second end of the shaft portion 274. The shaft portion 274 may taper at the second end to form the tip 276. The guide pin tissue protector 270 may also include a through hole or cannulation 278 extending from the first end to the second end to enable a guide wire (not shown) to pass through the tissue protector 270 and engage a patient's bone.

Referring now to FIGS. 35-52, another ankle fusion plate system 400 is shown. The fusion system 400 may include an implant, plate or bone plate 110, an alignment guide 410, and a fastener 450. The alignment guide 410 may be coupled to the plate 110 for insertion of the fastener 450 across a joint without contacting the fasteners or screws (not shown) inserted through the plate 110. The plate 110 is as described above with reference to FIGS. 3-10 and will not be described again here for brevity sake. Each component of the fusion system 400 may be made from, for example, a biocompatible material, including but not limited to a metal, polymer, composite, etc.

Figure 36:
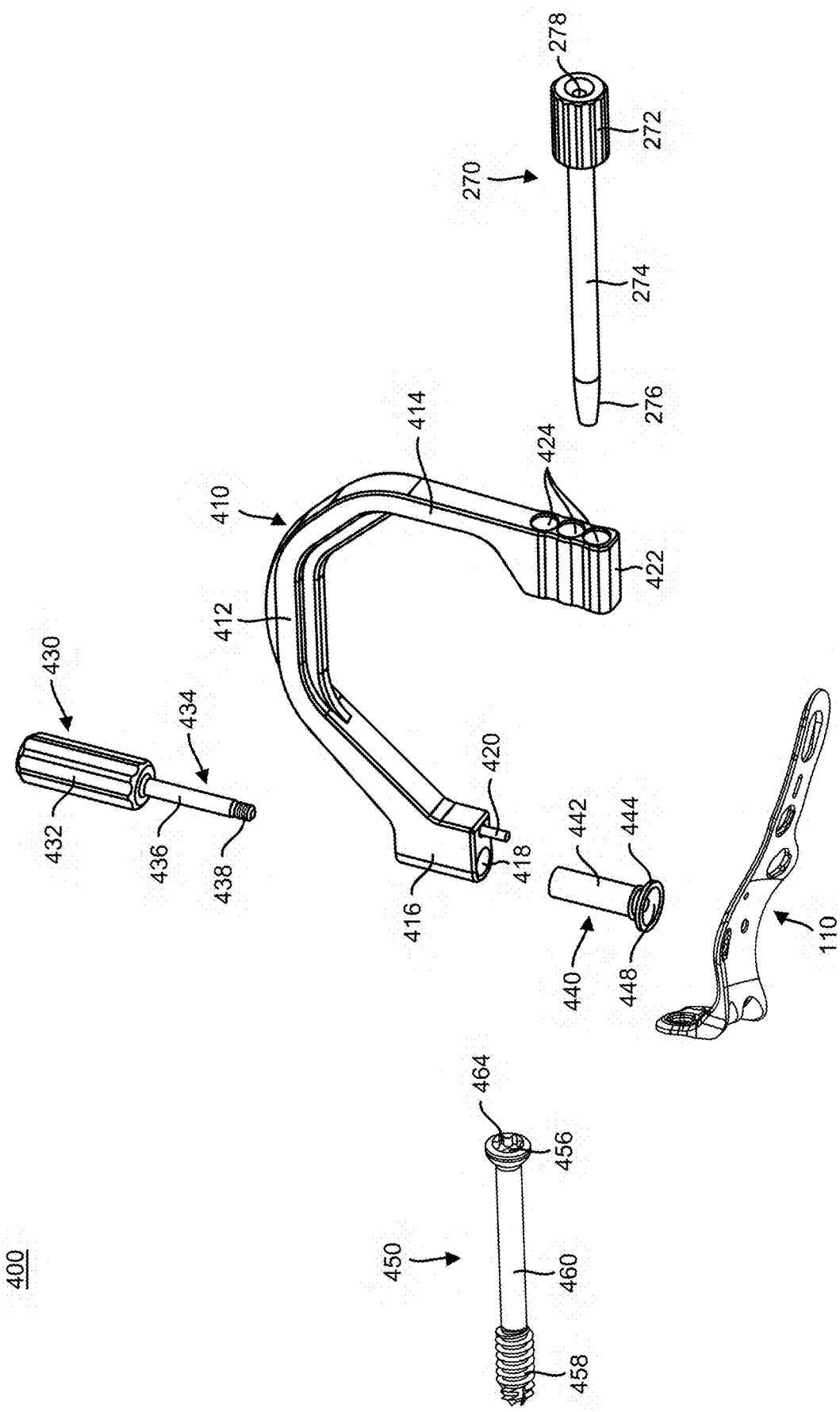
FIG. 36 is another exploded, perspective view of the fusion system of FIG. 35, in accordance with an aspect of the present disclosure.
Figure 37:
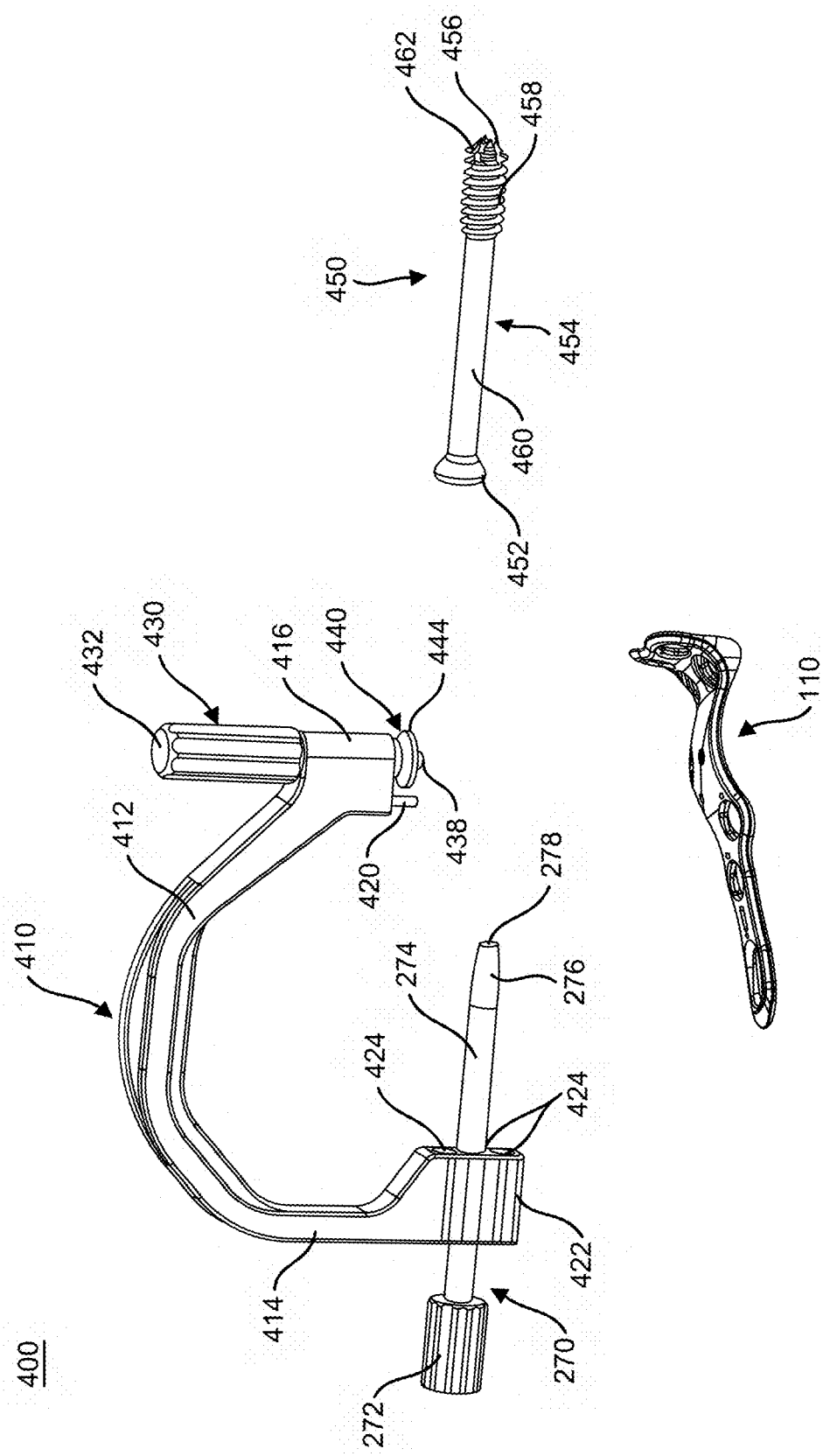
FIG. 37 is a top partially exploded perspective view of the fusion system of FIG. 35, in accordance with an aspect of the present disclosure.
Figure 38:
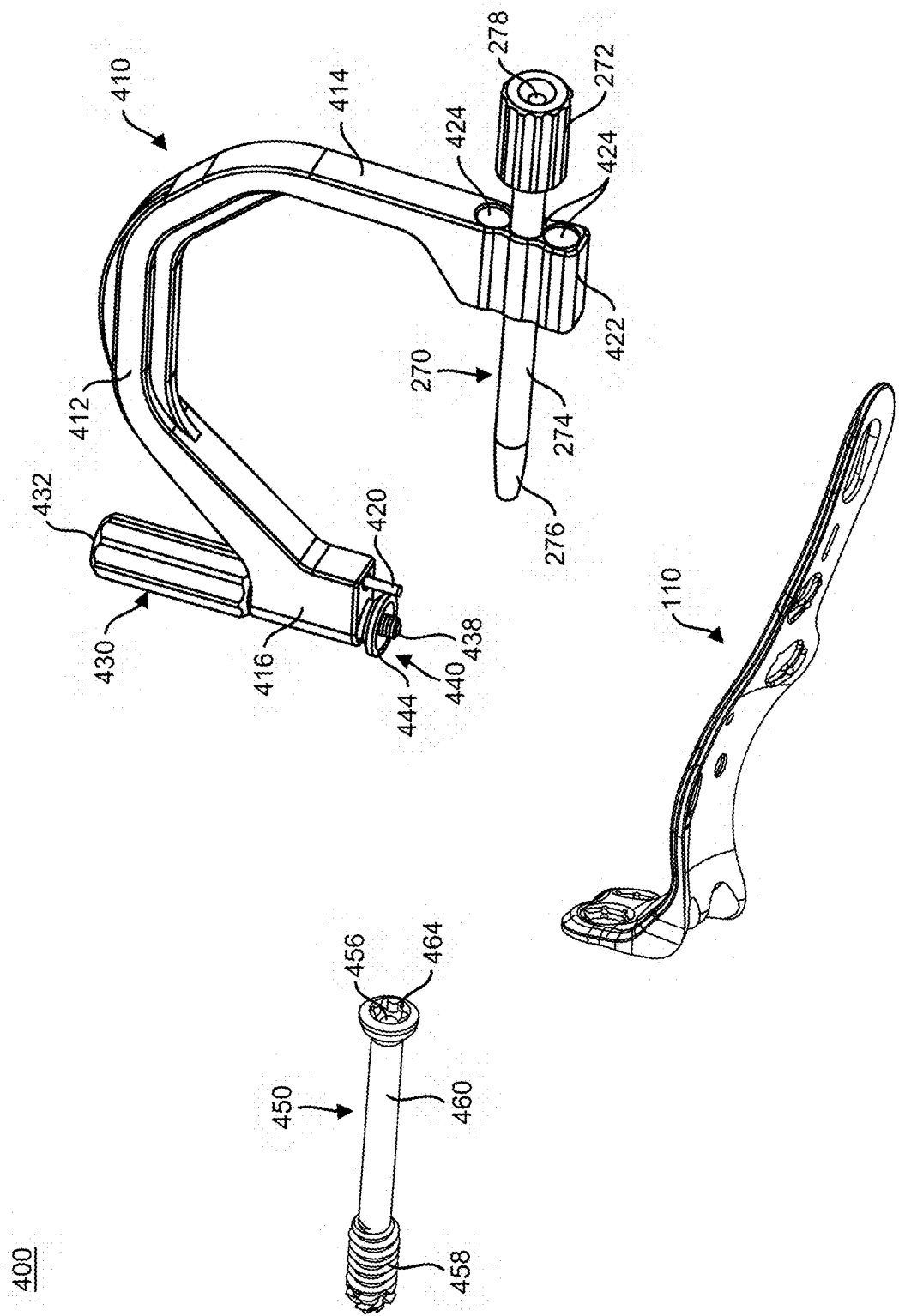
FIG. 38 is a bottom partially exploded perspective view of the fusion system of FIG. 35, in accordance with an aspect of the present disclosure.
Figure 39:
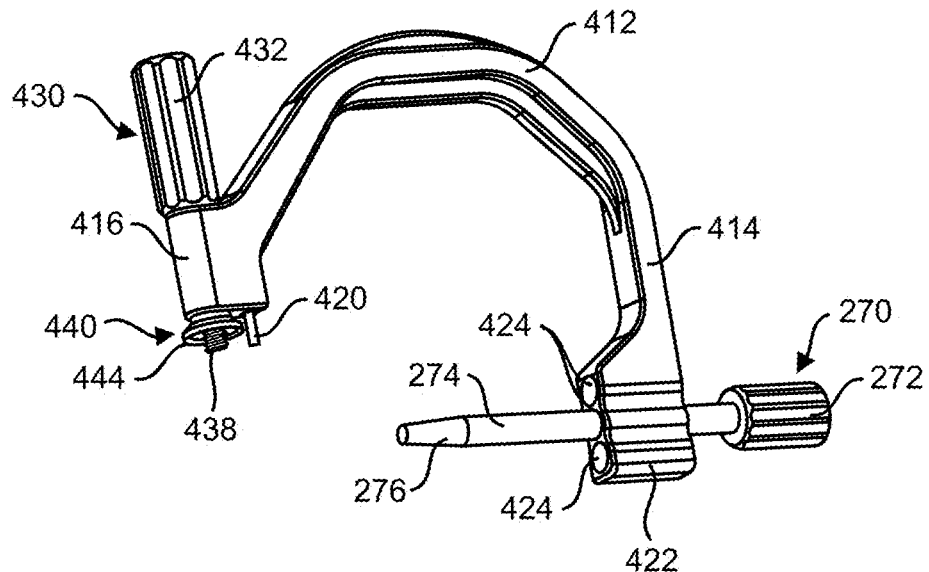
FIG. 39 is a first side, perspective view of the alignment guide of the fusion system of FIG. 1, in accordance with an aspect of the present disclosure.
Figure 40:
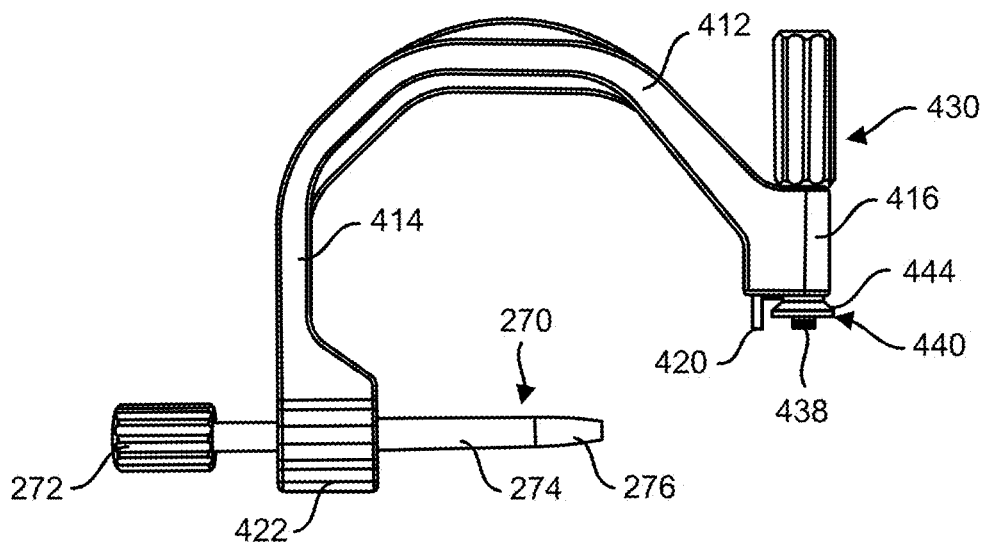
FIG. 40 is a first side view of the alignment guide of FIG. 39, in accordance with an aspect of the present disclosure.
Figure 41:
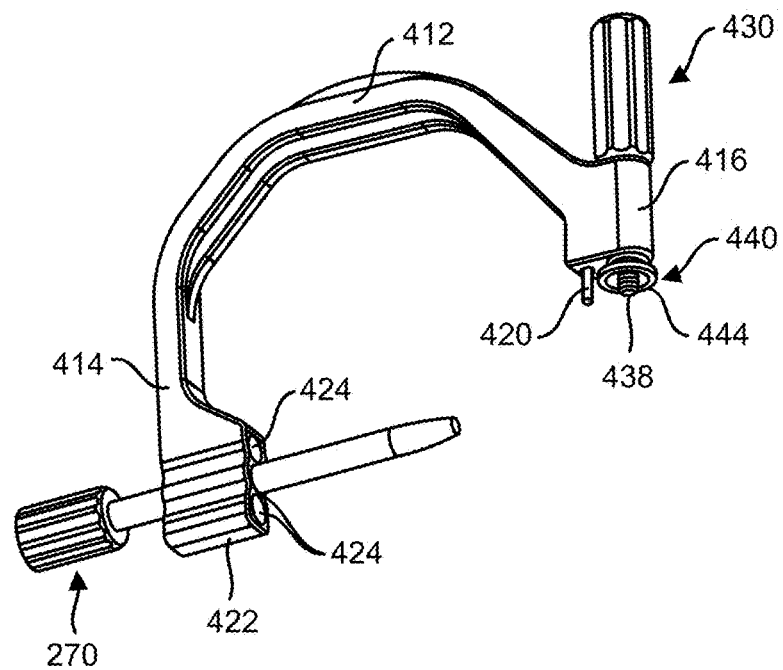
FIG. 41 is a second side, perspective view of the alignment guide of FIG. 39, in accordance with an aspect of the present disclosure.
Figure 42:
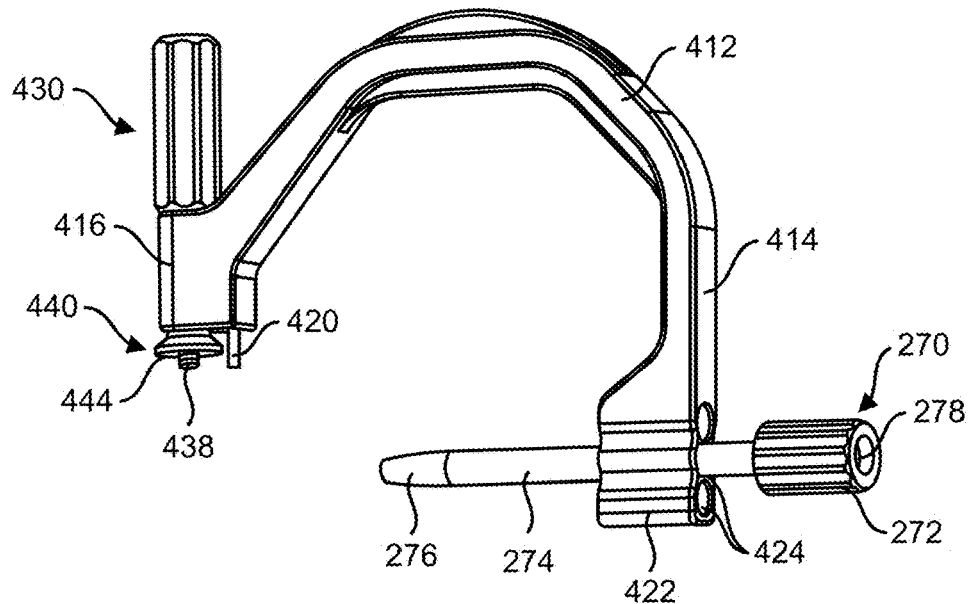
FIG. 42 is a first end, perspective view of the alignment guide of FIG. 39, in accordance with an aspect of the present disclosure.
Figure 43:
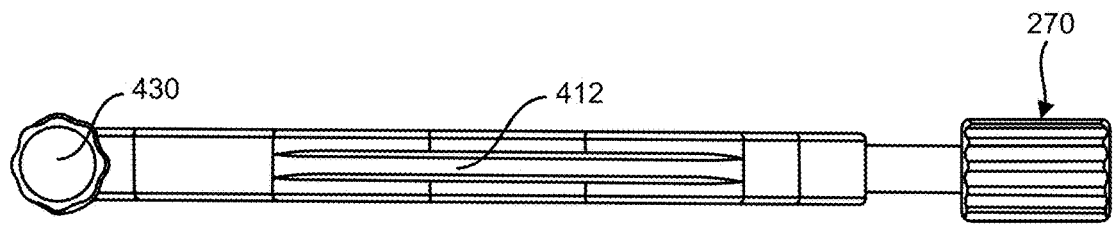
FIG. 43 is a top view of the alignment guide of FIG. 39, in accordance with an aspect of the present disclosure.
Figure 44:
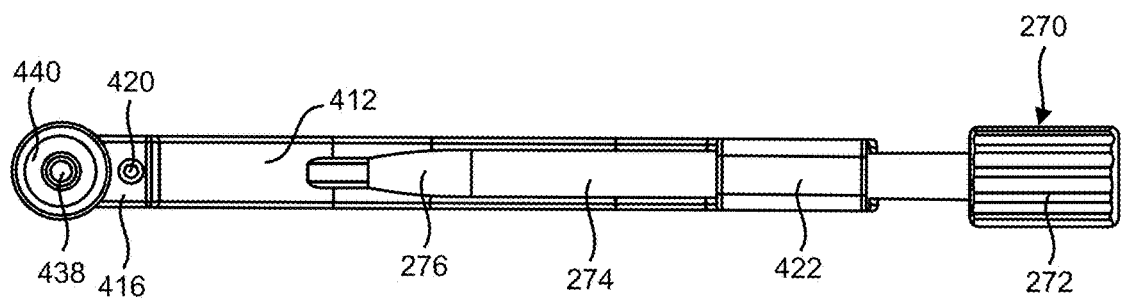
FIG. 44 is a bottom view of the alignment guide of FIG. 39, in accordance with an aspect of the present disclosure.
Figure 45:
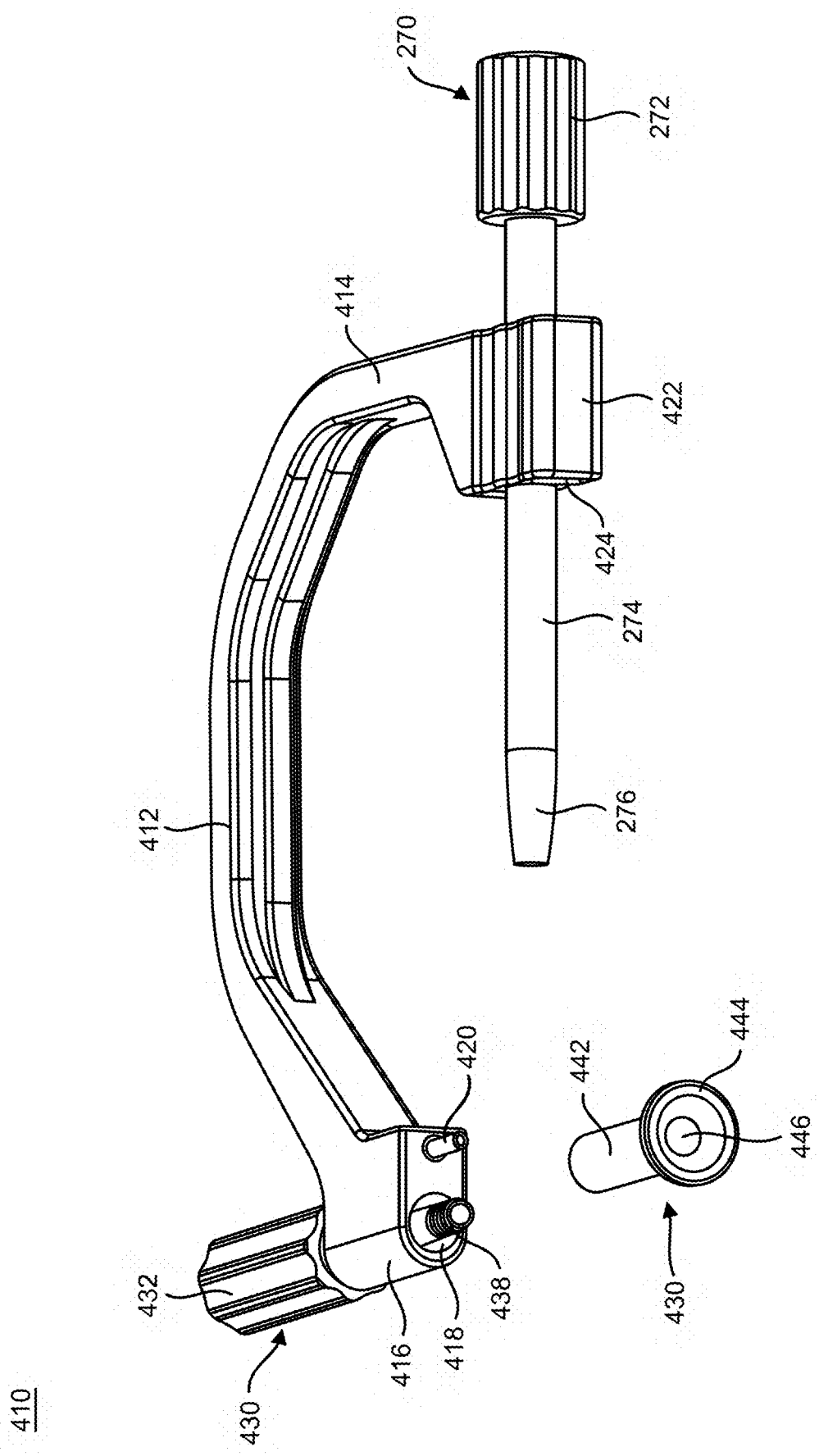
FIG. 45 is a partially exploded, bottom perspective view of the alignment guide of FIG. 39, in accordance with an aspect of the present disclosure.
Figure 46:
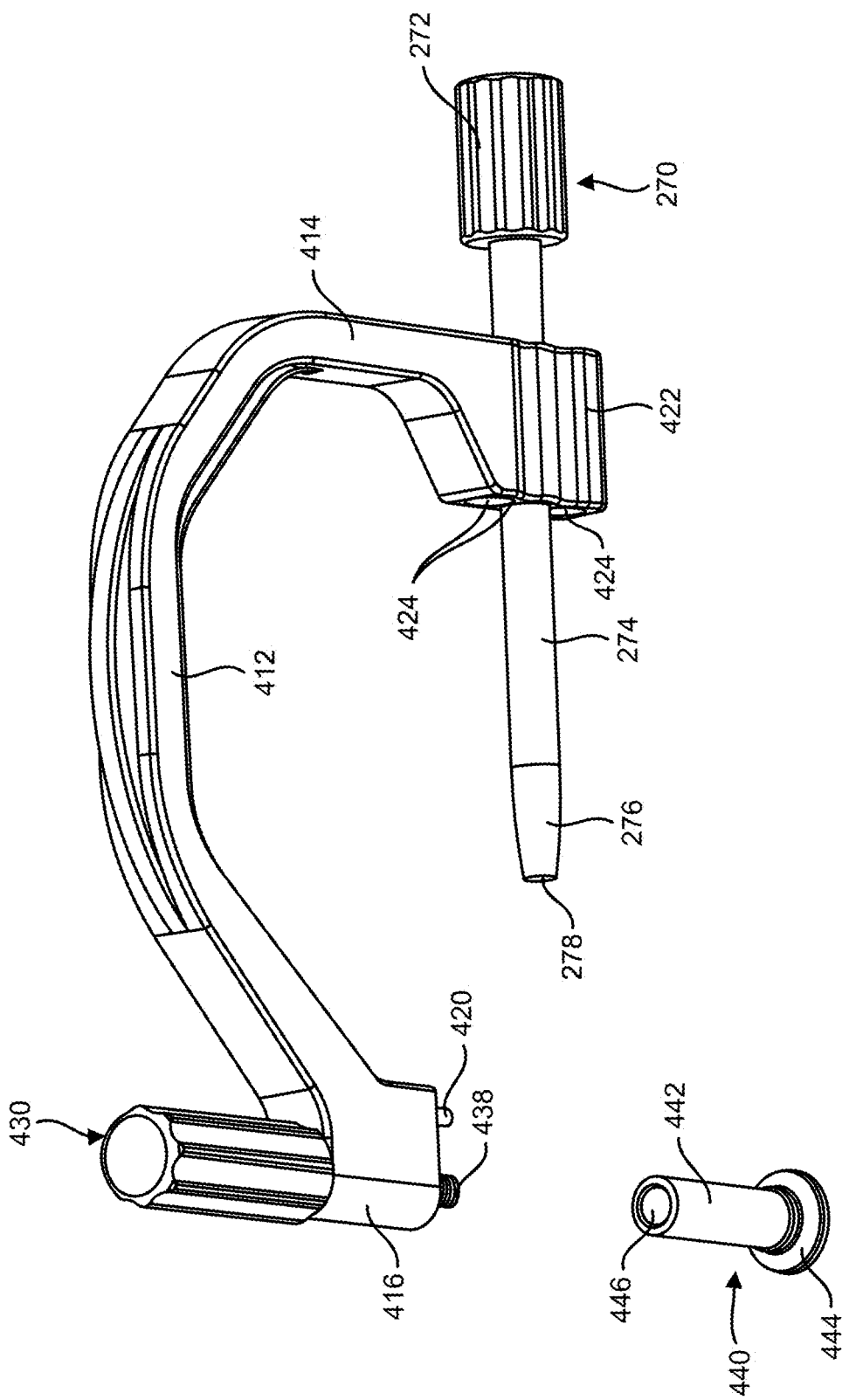
FIG. 46 is a partially exploded, top perspective view of the alignment guide of FIG. 39, in accordance with an aspect of the present disclosure.
Figure 47:
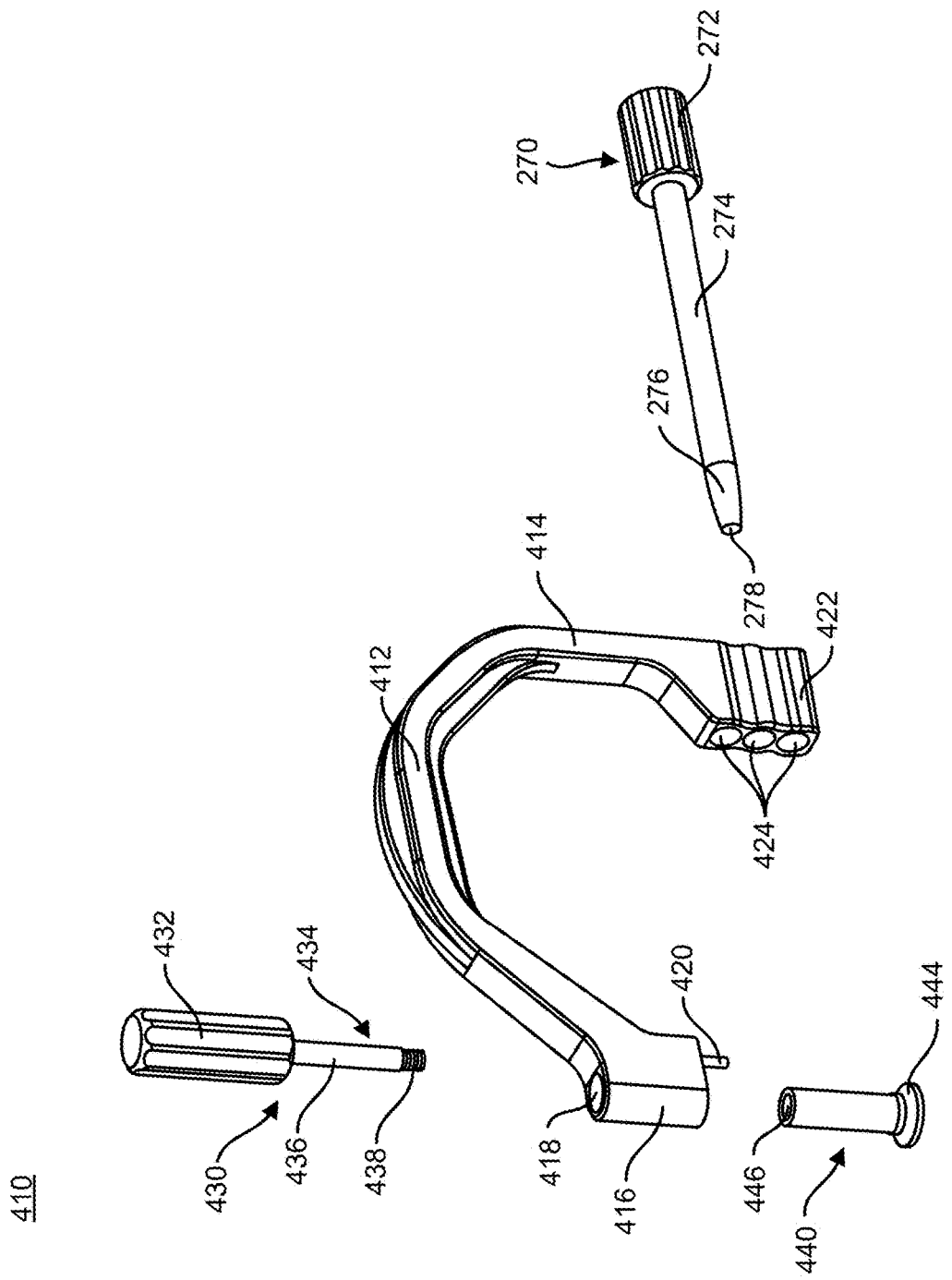
FIG. 47 is an exploded, top perspective view of the alignment guide of FIG. 39, in accordance with an aspect of the present disclosure.
Figure 48:
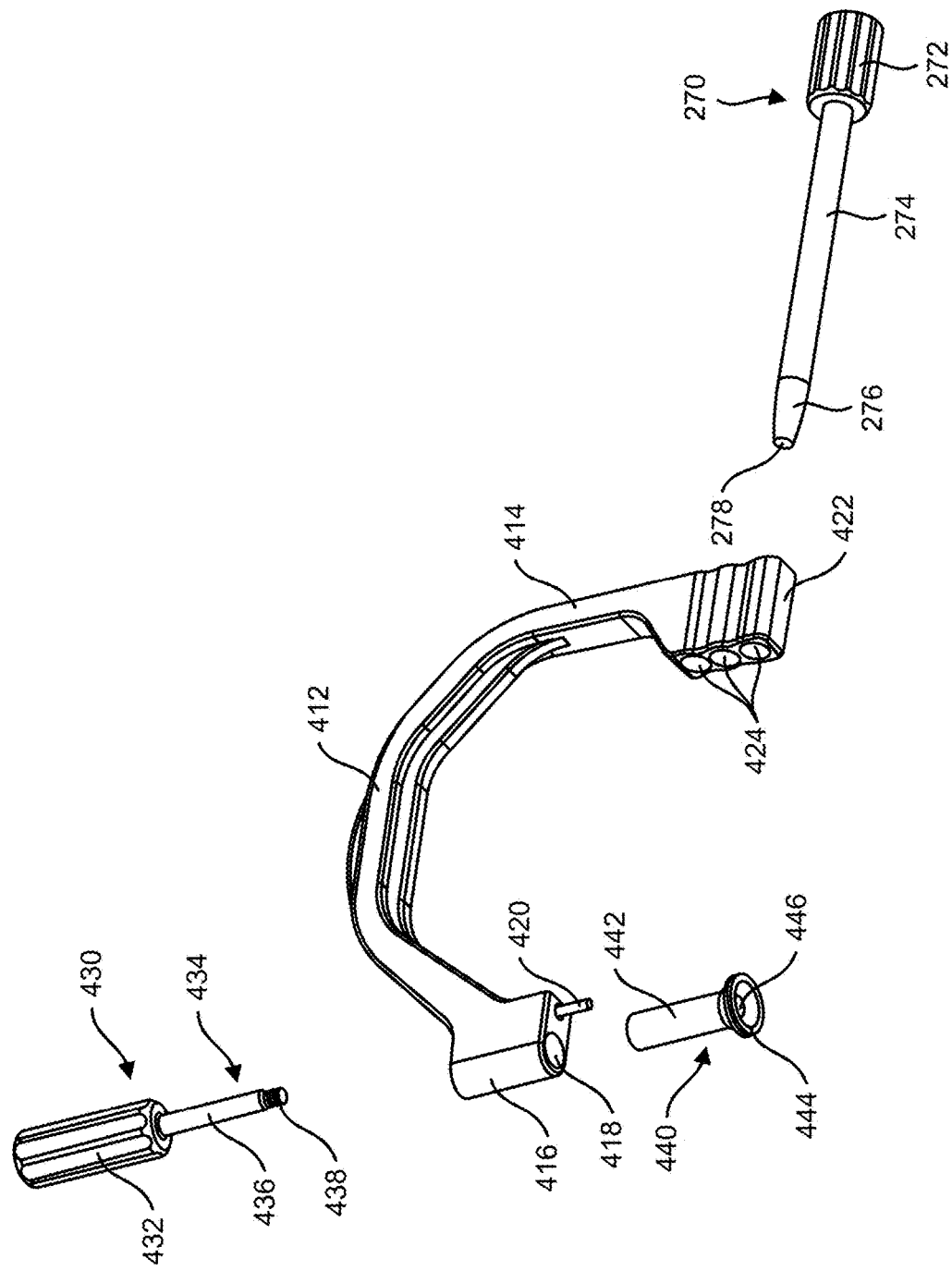
FIG. 48 is an exploded, bottom perspective view of the alignment guide of FIG. 39, in accordance with an aspect of the present disclosure.
Figure 49:
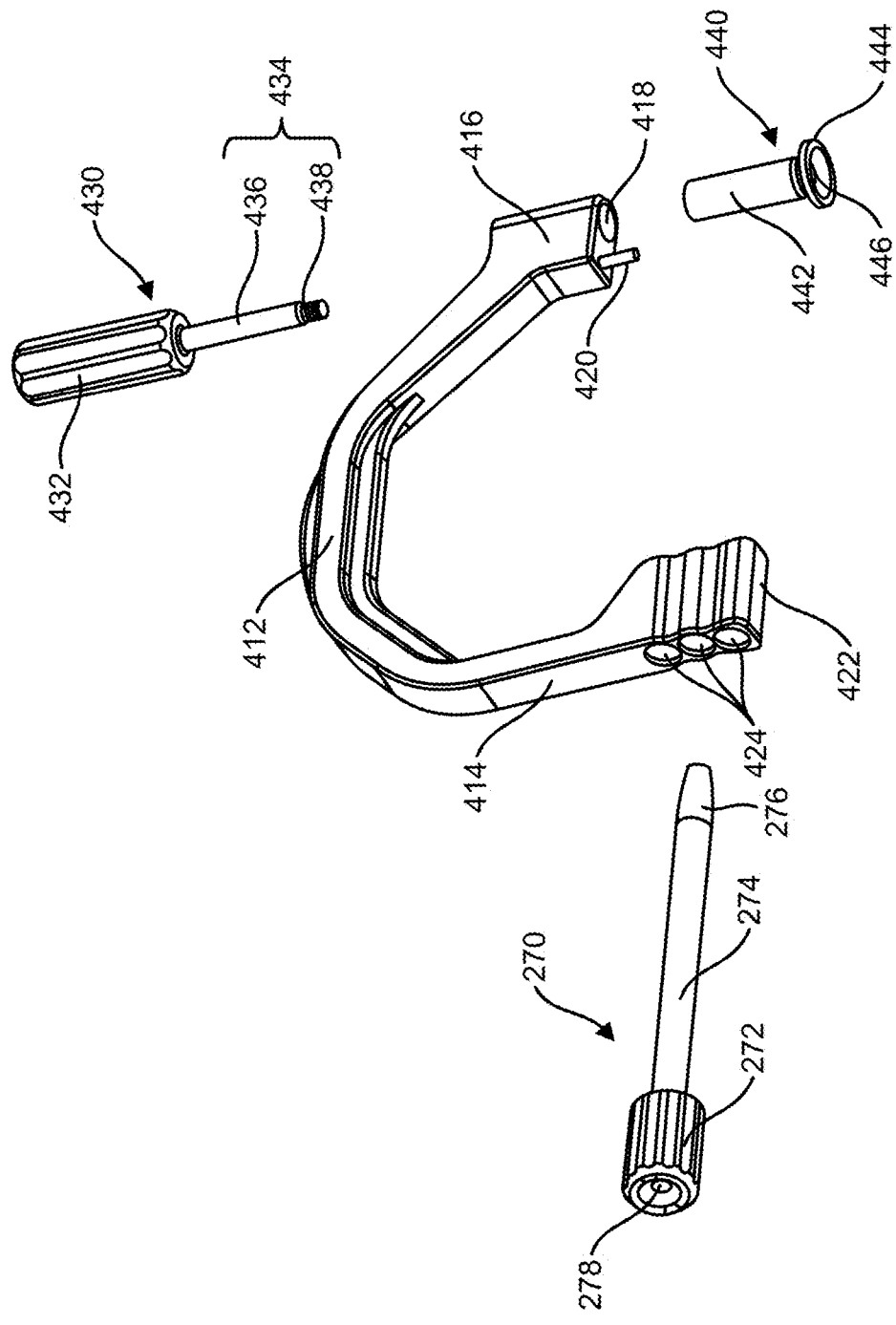
FIG. 49 is an exploded, first end perspective view of the alignment guide of FIG. 39, in accordance with an aspect of the present disclosure.
Figure 50:
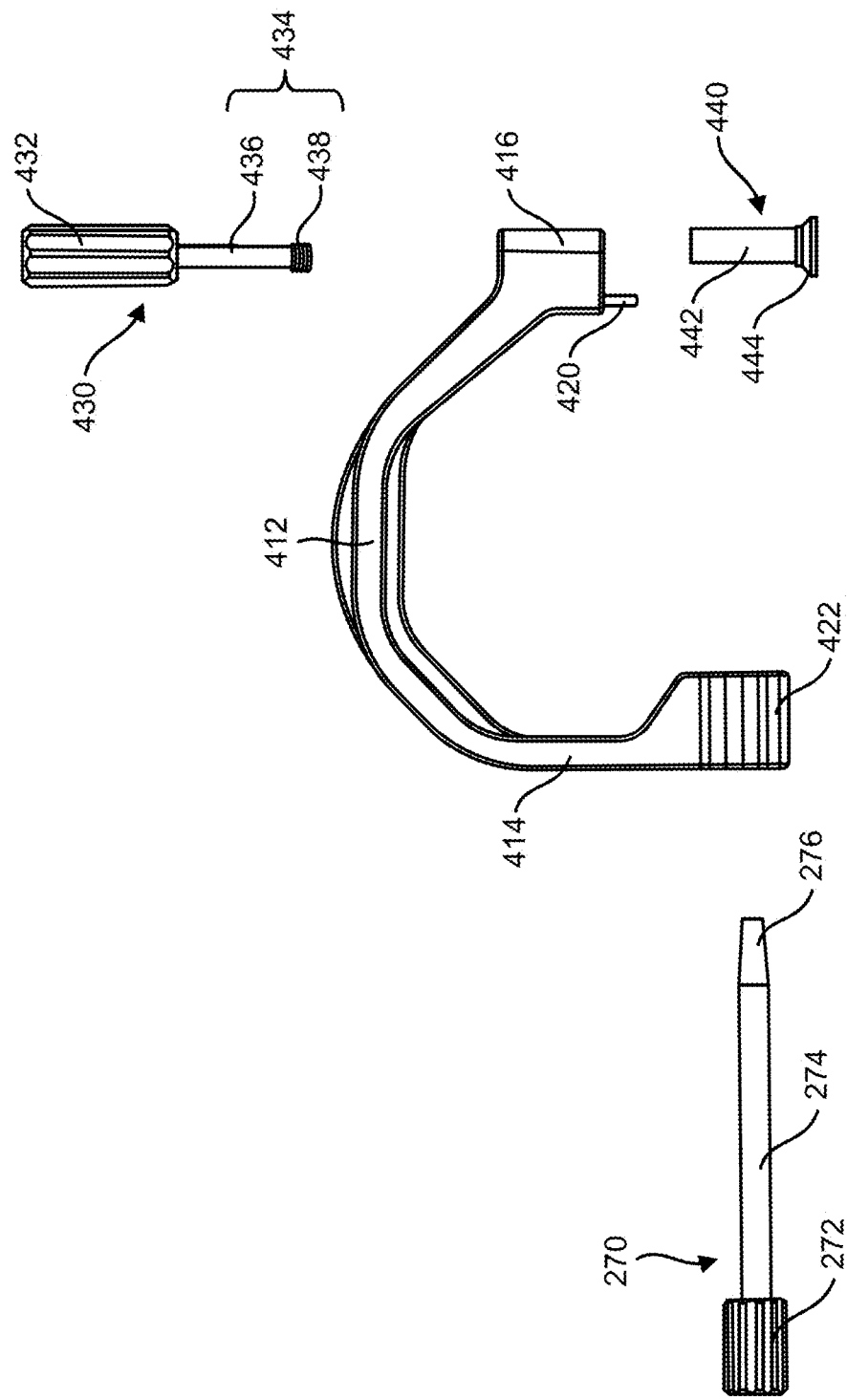
FIG. 50 is a side view of the alignment guide of FIG. 39, in accordance with an aspect of the present disclosure.

Referring now to FIGS. 35-38, the fastener 450 may be, for example, a compression screw, compression fastener, beam fastener, bone screw, beam screw, fixator, elongate member, rod, lag screw, headless screw, a solid screw, or screw for crossing a joint or fracture. The fastener or screw 450 may include a head portion 452 and a shaft or shank portion 454 extending away from a bottom surface of the head portion 452. The fastener 450 may also include a cannulation or through hole 456 extending from a first end through the head portion 452 and the shaft portion 454 to the second end. The cannulation 456 may be, for example, sized and shaped to receive a temporary fixation or guiding member, such as, a k-wire, guide wire, olive wire, pin, or the like, as known by one of ordinary skill in the art. As shown in FIGS. 36 and 38, the head portion 452 may include, for example, a drive feature 464 for receiving a drill or screw driver to insert the fastener 450 into a patient's bones. The shaft portion 454 of the fastener 450 may include, for example, a threaded portion 458 and a smooth portion 460 along the length of the shaft portion 454. The length of the threaded portion 458 and smooth portion 460 may, for example, vary depending on the bones the fastener 450 will be inserted into. In the depicted embodiment, the threaded portion 458 is shorter than the smooth portion 460. Alternatively, the shaft portion 454 may be, for example, threaded along its entire length. The shaft portion 454 may also include at least one tooth 462 positioned at the end of the shaft portion 454 to assist with insertion of the fastener 450 into a patient's bones.

Referring now to FIGS. 39-50, the alignment guide or bone plate alignment guide 410 is shown. The alignment guide 410 may include a body 412, a fixation member 430, a coupling member 440, and a guide pin tissue protector 270. The fixation member 430 and coupling member 440 may be received in a first end of the body 412 and the guide pin tissue protector 270 may be received in a second end of the body 412. The alignment guide 410 may also include at least one guide wire or pin (not shown) for insertion through the guide pin tissue protector 270.

As shown in FIGS. 47-50, the body 412 may include an arm 414 with an attachment portion 416 at the first end of the body 412 and an alignment portion 422 at the second end of the body 412. The attachment portion 416 may include a through hole 418 extending through the attachment portion 416 near the first end. The attachment portion 416 may also include a peg or alignment pin 420 extending away from a bottom surface of the attachment portion 416. The through hole 418 may be positioned adjacent to the alignment pin 420. The alignment pin 420 may be, for example, sized and shaped to engage the alignment opening 140 of the plate 110. The bottom surface of the attachment portion 416 may be, for example, a flat surface for engaging the coupling member 440.

The alignment portion 422 may include at least one hole 424, as shown in FIGS. 35-39, 41, 42, and 47-49. The alignment portion 422 may include at least one hole 424. The at least one hole 424 may be, for example, three holes 424, as shown in the depicted embodiment. The three holes 424 may be positioned linearly as the alignment portion 422 extends away from the arm 414. The holes 424 may be, for example, straight or angled to a desired insertion position as the holes 424 extend through the arm 414 of the body 412. In the depicted embodiment, the holes 424 extend through the alignment portion 422 parallel to each other. The holes 424 may be, for example, sized and shaped to receive the shaft portion 274 of the guide pin tissue protector 270.

As shown in FIGS. 35, 36 and 47-50, the fixation member 430 may include a knob 432 and a shaft 434 extending away from a bottom surface of the knob 432. The shaft 434 may include a first portion 436 extending away from the knob 432 and at least one engagement member 438 for coupling to the engagement opening 138 of the plate 110. The at least one engagement member 438 may be, for example, positioned at an end of the first portion 436 opposite the knob 432. The engagement member 438 may be, for example, threaded to engage corresponding threads in the opening 138 of the plate 110 as shown in the depicted embodiment, deformable to be removeably press fit into the opening 138 in the plate 110, or another similar configuration that achieves a coupling of the alignment guide 410 to the plate 110.

With continued reference to FIGS. 35, 36 and 47-50, the coupling member 440 includes a shaft 442 and a head 444 positioned at a first end of the coupling member 440. The head 444 may have, for example, an outer diameter that is larger than the outer diameter of the shaft 442. A bottom surface of the head portion 444 of the coupling member 440 may be, for example, curved, arced, or otherwise shaped to match the shape of a top surface of the plate 110 where the head portion 444 engages the plate 110. The coupling member 440 may also include a through hole 446 extending through the coupling member 440 along the longitudinal axis. As shown in FIGS. 36, 38, 41, 44, and 45, the coupling member 440 may also include a recessed region 448 extending into the head 444 from the first end. The exterior diameter of the shaft 442 of the coupling member 440 corresponds to the interior diameter of the through hole 418 of the alignment guide 410. Further, the exterior diameter of the first portion 436 of the fixation member 430 may correspond to the interior diameter of the through hole 418 of the alignment guide 410 allowing for the shaft 434 of the alignment guide 410 to pass through the through hole 446 of the coupling member 440. In addition, the exterior diameter of the head 444 of the coupling member 440 may have, for example, a diameter larger than the diameter of the through hole 418 of the alignment guide 410.

Referring now to FIGS. 23-34, one embodiment of a surgical method of using the fusion system 100, 400 is shown. The method may include exposing a joint 308 and preparing the joint 308. Exposing the joint 308 may include making an incision, for example, a longitudinal midline incision over the anterior ankle, beginning approximately 10 cm proximal to the ankle joint 308 and terminating just distal to the talonavicular joint 300. The incision may start approximately 1 cm lateral to the tibial crest just lateral to the tibialis anterior tendon. Exposing the joint 308 may include, for example, making an initial incision through the skin only. Next, the superficial peroneal nerve should be identified and retracted laterally. The surgeon should then continue to expose the joint 308 to the extensor retinaculum. Once the extensor retinaculum is exposed, the extensor hallucis longus (EHL) tendon may be identified below the retinaculum and the retinaculum should be divided longitudinally over the extensor hallucis longus tendon, which leaving the sheath of the tibialis anterior (TA) tendon intact. Then, the EHL tendon may be retracted laterally and the TA tendon medially. In addition, exposing the joint 308 may include continuing exposure until the anterior capsule is visualized. Next, an anterior capsulotomy via a longitudinal incision may be performed and the capsule and periosteum may be elevated over the anterior tibia 306 and talus 302 to expose the anterior ankle joint, the tibial plafond, the medial and lateral gutters and the anterior and dorsal talus. Next, any osteophytes on the tibia 306 and talus 302 may be removed to allow for exposure to the ankle joint and facilitate entry of instrumentation for cartilage removal. The method may then include joint preparation, for example, of the tibiotalar joint 308 based on surgeon preference, as known by one of ordinary skill in the art.

Figure 23:
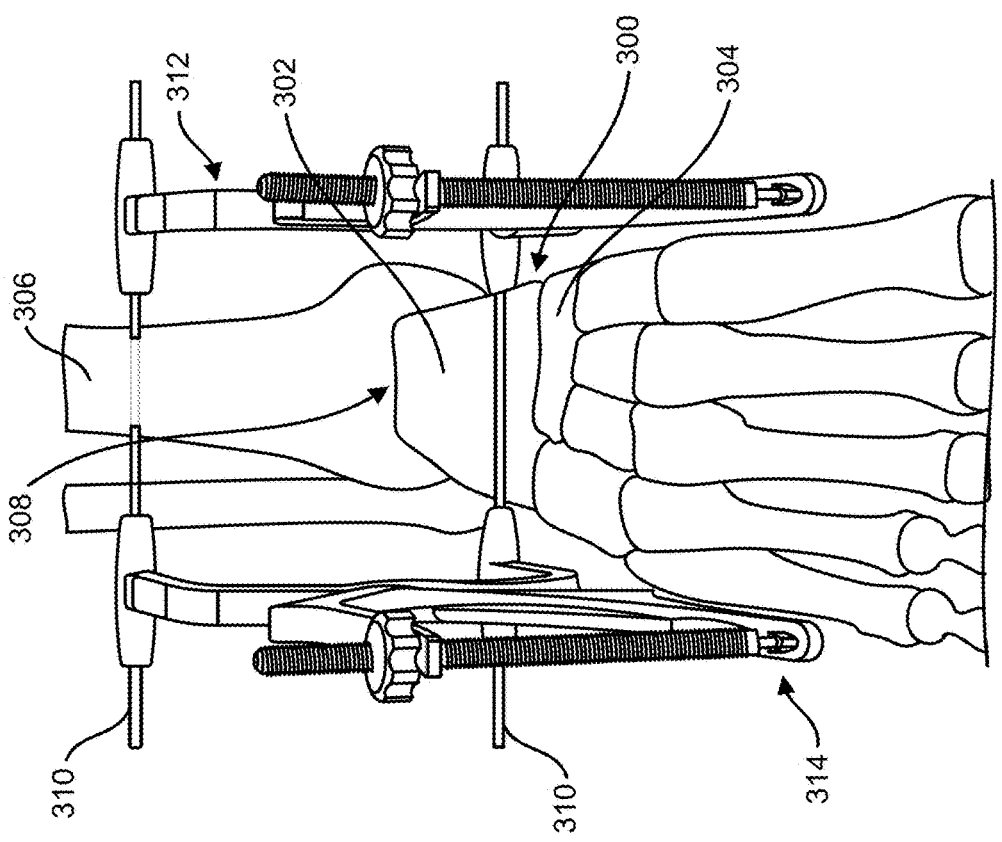
FIG. 23 is an anterior view of a portion of a patient's leg and foot with a compression system coupled to the bones, in accordance with an aspect of the present disclosure.

As shown in FIG. 23, the method may then optionally include temporarily fixing the ankle joint 308. The joint 308 may be fixed by placing k-wires or other fasteners across the joint 308. Alternatively, a wire 310 may be placed bi-cortically across the tibia 306. A second wire 310 may be placed bi-cortically across the talus 302. Then, a first compressor 312 may be slid onto two wires 310 from a medial side. Then, a second compressor 314 may be slid onto the two wires 310 from a lateral side. A force may be applied to each side of the compressors 312, 314 until adequate compression is achieved across the tibiotalar joint 308 and varus/valgus orientation is correct. Next, k-wires (not shown) may be placed across the tibiotalar joint 308 to maintain the position and compression, if necessary. Alternatively, two wires 310 may be placed unicortically into the tibia 306, medially and laterally, respectively. The two wires 310 may be placed unicortically into the talus 302, medially and laterally, respectively. The first compressor 312 may be slid onto the two medial wires 310 and the second compressor 314 may be slid onto the lateral wires 310. The compression of the tibiotalar joint 308 may be achieved as described above.

Figure 24:
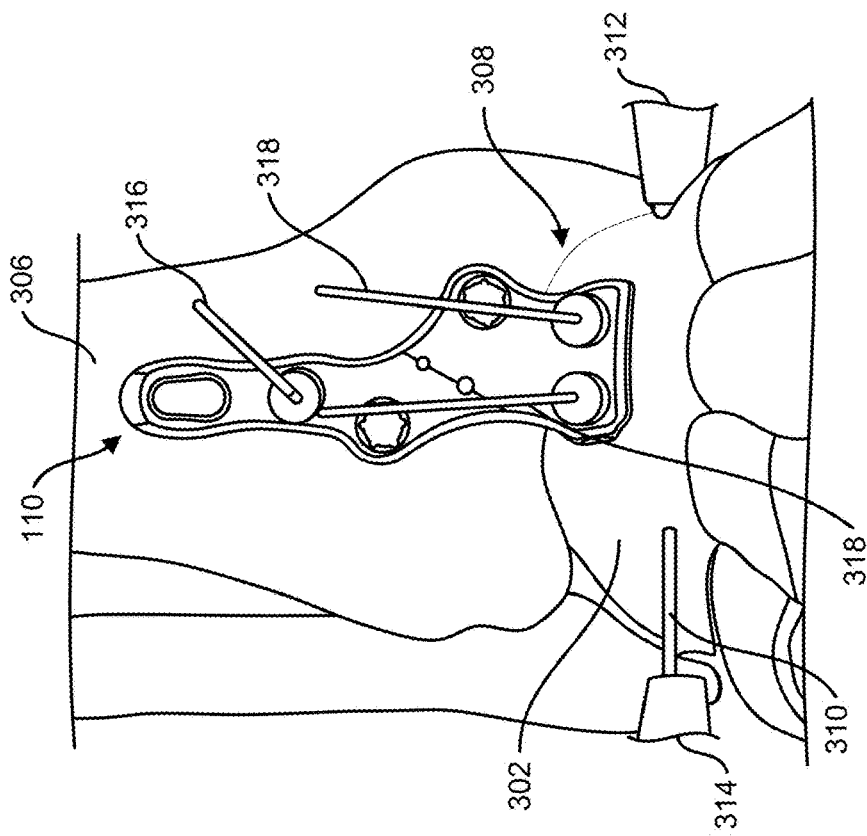
FIG. 24 is an anterior view of the bones of FIG. 23 with the plate of FIG. 3 positioned over a joint and temporarily secured to the patient's bones, in accordance with an aspect of the present disclosure.

Referring now to FIG. 24, the method may then include obtaining a fusion plate 110. The proximal aspect of the plate 110 may be centered over the tibia 306 and the distal portion of the plate 110 will be located slightly medial to midline. Next, the method may include securing the plate 110 to the anterior aspect of the tibiotalar joint 308 using a temporary fixator 316, for example, a long olive wire in the tibia and temporary fixators 318, for example, short olive wires in the distal holes of the talus 302. After the plate 110 is temporarily secured to the bones 302, 306, the position of the plate 110 may be confirmed using fluoroscopy.

Figure 26:
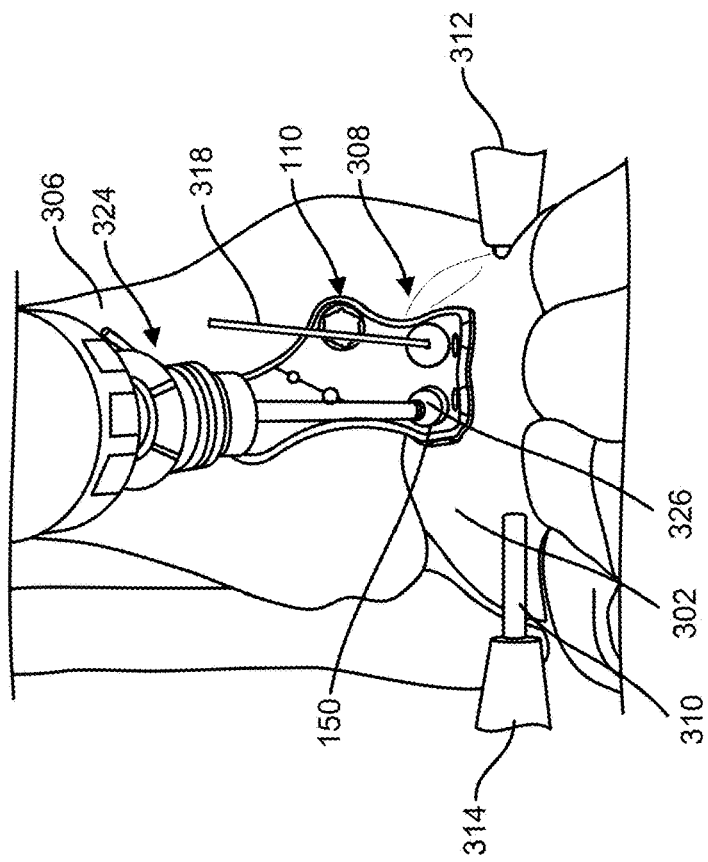
FIG. 26 is an anterior view of the bones of FIG. 25 after removal of the drill and drill guide and with a screw driver inserting a first screw through the plate of FIG. 3 and into at least one bone, in accordance with an aspect of the present disclosure.
Figure 25:
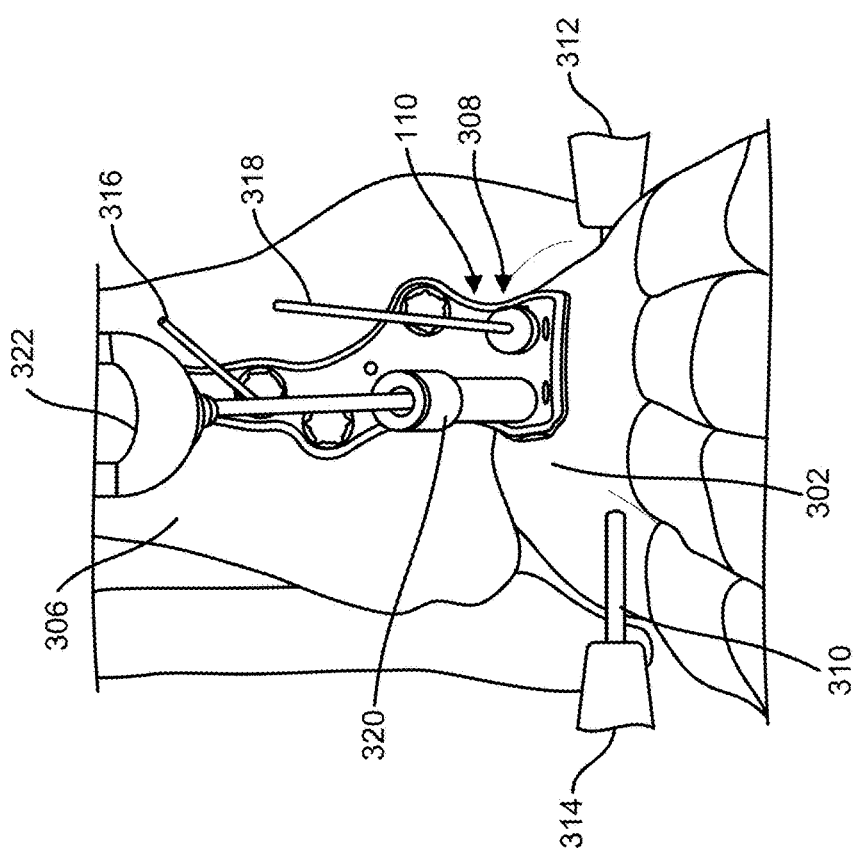
FIG. 25 is an anterior view of the bones of FIG. 24 with one temporary fixator replaced by a drill guide coupled to the plate of FIG. 3 and a drill inserted through the drill guide and into at least one bone, in accordance with an aspect of the present disclosure.
Figure 27:
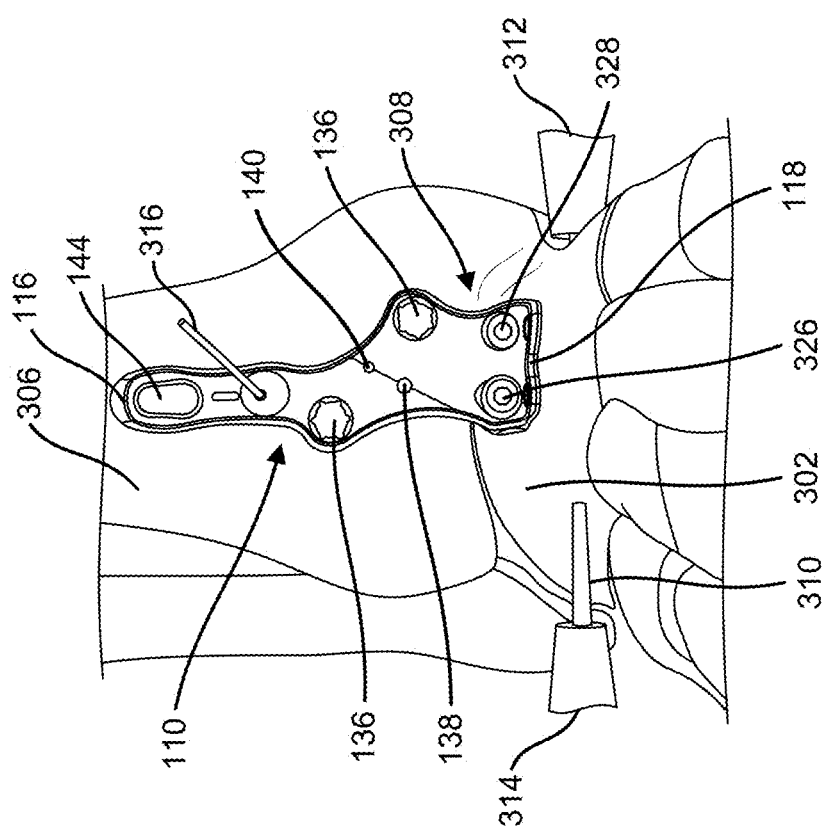
FIG. 27 is an anterior view of the bones of FIG. 26 after insertion of a second screw through the plate of FIG. 3 and into at least one bone, in accordance with an aspect of the present disclosure.

Referring now to FIG. 25, the method may also include preparing the talus 302 for inserting screws 326, 328 (See FIGS. 27-29 and 31-34) through the fourth through holes 150 in the plate 110. As shown in FIG. 26, the method may include obtaining a drill guide 320 and inserting the drill guide 320 into a fourth through hole 150 positioned on the lateral side. Next, a drill 322 may be inserted through the drill guide 320 and into the talus 302. After drilling an opening in the talus 302, the drill 322 and drill guide 320 may be removed from the lateral through hole 150 and a depth gauge (not shown) may be inserted into the drilled opening to measure the screw length for insertion into the drilled opening. Once the screw length is determined, a first screw 326 may be inserted through the lateral through hole 150 and into the talus 302 using, for example, a screw driver 324. The first screw 326 may be, for example, partially inserted into the lateral hole 150 until the second screw 328 is inserted into the medial hole 150. As shown in FIG. 27, the method may include inserting the second screw 328 through the medial hole 150 in the plate 110 and into the talus 302, as described above with respect to the insertion of the first screw 326. Once the first and second screws 326, 328 are both partially inserted through the plate 110, the screws 326, 328 may then be fully tightened and seated to secure the plate 110 to the talus 302.

Figure 28:
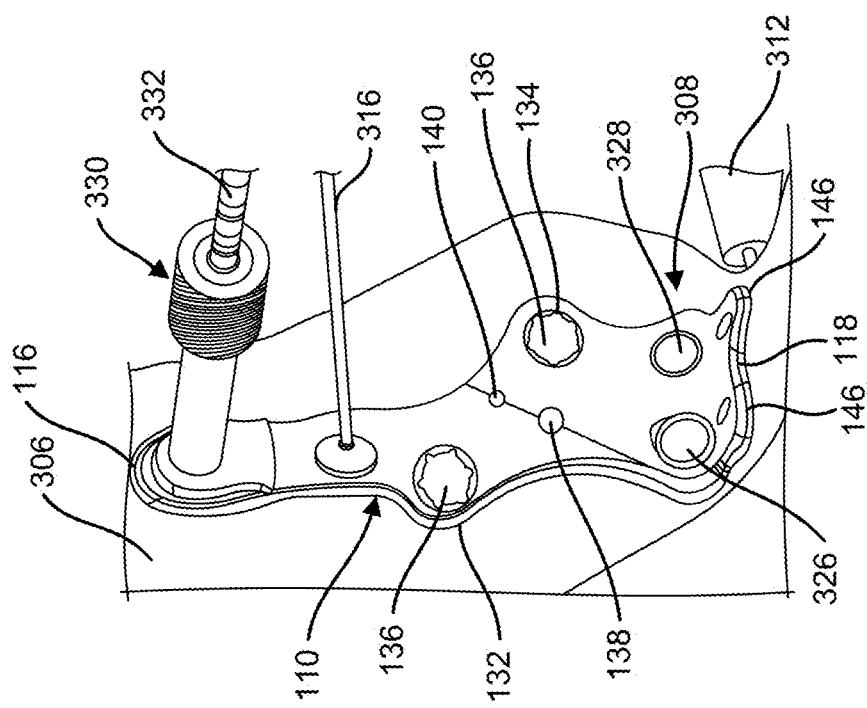
FIG. 28 is an anterior view of the bones of FIG. 27 after coupling a compression slot drill guide to the slot of the plate of FIG. 3 and inserting a drill through the compression slot drill guide and into at least one bone, in accordance with an aspect of the present disclosure.
Figure 29:
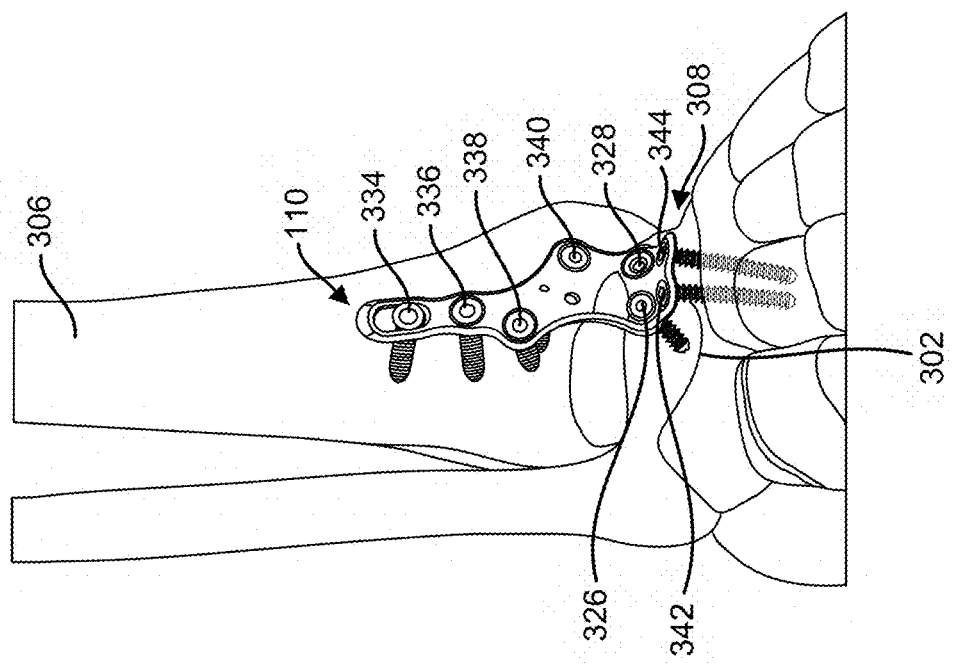
FIG. 29 is a perspective view of the bones of FIG. 28 after removal of the drill and compression slot drill guide and insertion of a compression screw and five additional screws through the plate of FIG. 3 and into at least one bone, in accordance with an aspect of the present disclosure.

Referring now to FIG. 28, the method may also include obtaining a compression slot drill guide 330 and inserting the drill guide 330 into the slot 144 of the plate 110 on the tibia 306. The drill guide 330 may include, for example, an arrow which may point toward the tibiotalar joint 308. Next, a drill 332 may be inserted through the drill guide 330 and an opening may be drilled into the tibia 306. The method may further include removing the drill guide 330 from the plate 110 and measuring the drilled opening with a depth gauge to determine the screw length for the compression screw 334. The compression screw 334 may then be inserted through the slot 144 until fully seated, as shown in FIG. 29. Next, the remaining holes 136, 142 may be prepared as described in greater detail above to receive screws 336, 338, 340 for insertion into the tibia 306. Then, the two compressors 312, 314 and wires 310 may be removed from the bones 302, 306. The method may further include inserting screws 342, 344 through the third through holes 148 of the plate 110 and into the talus 302 using the method described in greater detail above, which will not be described again here for brevity sake.

Figure 30:
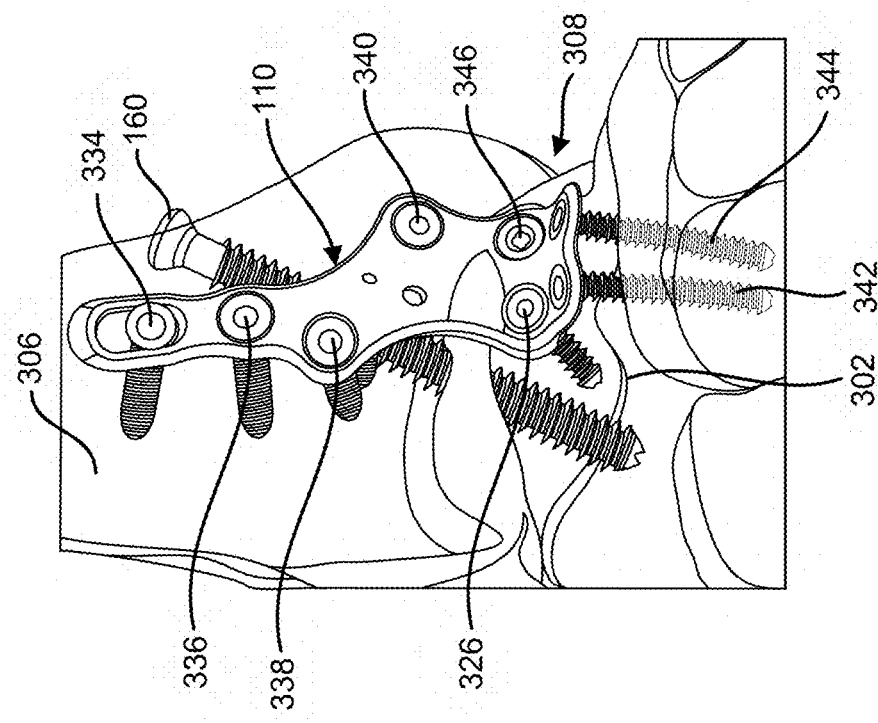
FIG. 30 is an enlarged, anterior view of the bones of FIG. 29 with a screw replaced by a plate washer and a fastener of the fusion system of FIG. 1 inserted across a joint, in accordance with an aspect of the present disclosure.

Referring now to FIG. 30, the method may optionally include inserting a plate washer or washer 346 in place of at least one screw 326, 328, 336, 338, 340, 342, 344. The plate washers may be used if the talus is flattened or there are inconsistencies in the tibia. As shown in FIG. 30, a washer 346 may be inserted into the medial through hole 150 in place of the second screw 328. If a washer 346 is used, the washer 346 should be completely tightened to fully seat and lock the washer 346 within the screw hole 150.

Figure 31:
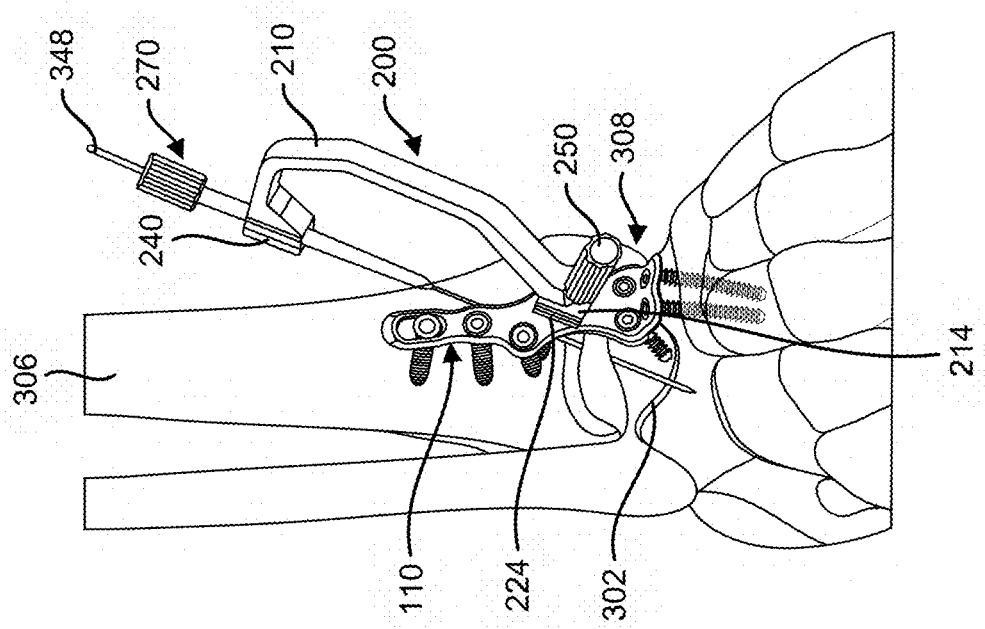
FIG. 31 is a perspective view of the bones of FIG. 29 after the alignment guide of FIG. 11 is coupled to the plate of FIG. 3 and a guide wire is inserted through the alignment guide and across the patient's joint, in accordance with an aspect of the present disclosure.

As shown in FIG. 31, the method may also include inserting a fastener 160 across the joint 308. With respect to the fastener 160, the terms "fastener," "crossing screw," "bone screw," "fixator," and "screw" may be used interchangeably herein as they essentially describe the same type of device. Inserting the crossing screw 160 may include obtaining an alignment guide 200 and coupling the alignment guide 200 to the plate 110. Alternatively, it is also contemplated that the alignment guide 200 may be coupled to the plate 110 prior to temporarily fixing the plate 110 to the bones 302, 306 to allow for use of a partially threaded screw to be placed prior to plate fixation to achieve compression across the joint via a partially threaded screw. After coupling the alignment guide 200 to the plate 110, the method may include inserting the guide pin tissue protector 270 through the desired hole 242 in the alignment portion 240 of the body 210. The body 210 may then be rotated with respect to the rotation member 224 coupled to the plate 110 to adjust the angle and start point of the fastener 160. Once the desired angle and start point of the fastener 160 is established, the fixation member 250 may be tightened to set and lock the position of the body 210 relative to the rotation member 224.

Figure 51:
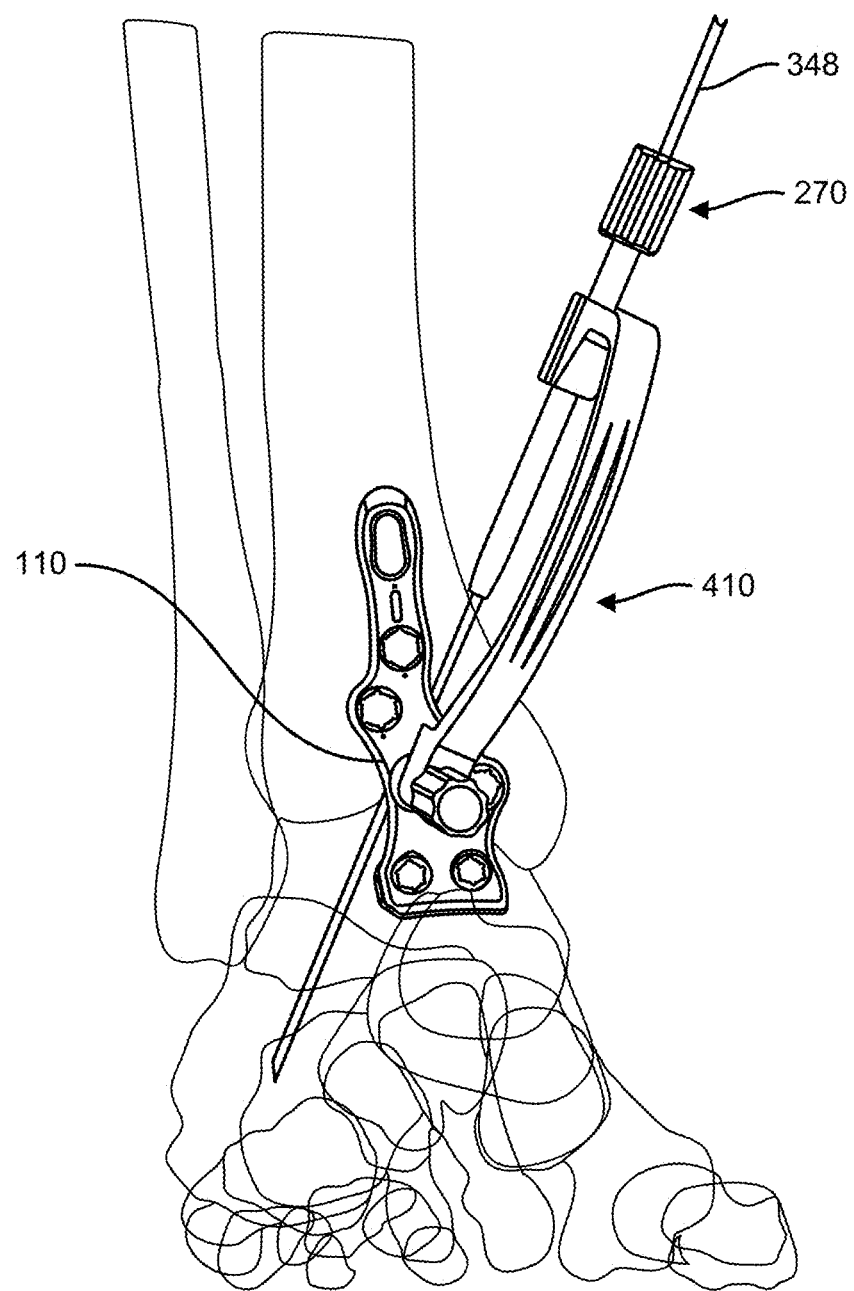
FIG. 51 is a perspective view of the bones of FIG. 29 after the alignment guide of FIG. 35 is coupled to the plate of FIG. 3, in accordance with an aspect of the present disclosure.
Figure 52:
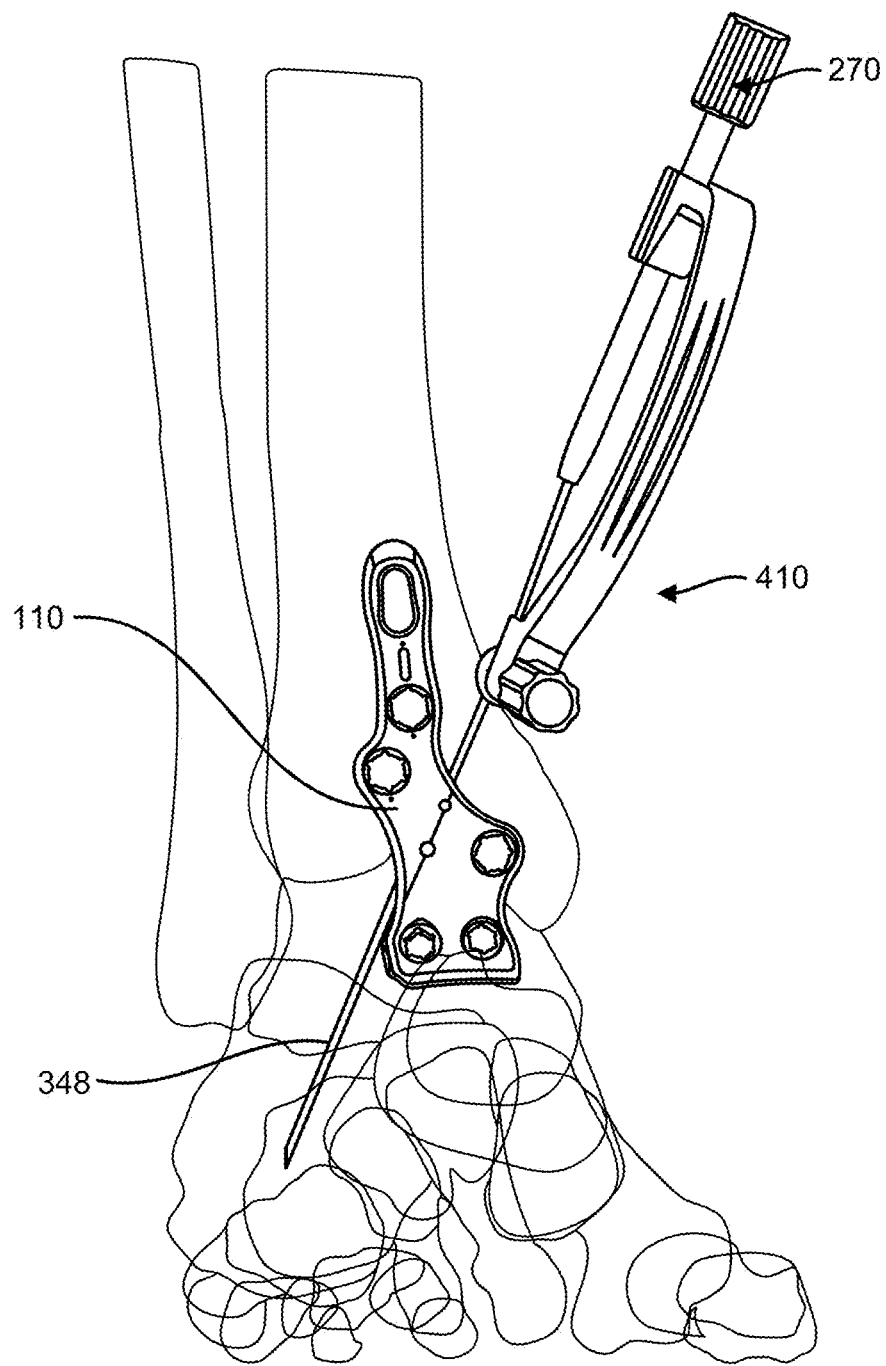
FIG. 52 is a perspective view of the bones of FIG. 51 as the alignment guide of FIG. 35 is being removed from the plate and guide wire, in accordance with an aspect of the present disclosure.

In another embodiment, as shown in FIGS. 51-52, the method may also include inserting a fastener 450 across the joint 308. With respect to the fastener 450, the terms "fastener," "crossing screw," "bone screw," "fixator," and "screw" may be used interchangeably herein as they essentially describe the same type of device. Inserting the crossing screw 450 may include obtaining an alignment guide 410 and coupling the alignment guide 410 to the plate 110. Alternatively, it is also contemplated that the alignment guide 410 may be coupled to the plate 110 prior to temporarily fixing the plate 110 to the bones 302, 306 to allow for use of a partially threaded screw to be placed prior to plate fixation to achieve compression across the joint via a partially threaded screw. After coupling the alignment guide 410 to the plate 110, the method may include inserting the guide pin tissue protector 270 through the desired hole 424 in the alignment portion 422 of the body 412.

The methods may then include inserting a wire 348 through the tissue protector 270 and across the arthrodesis site in the bones 302, 306. After inserting the wire 348 across the joint 308, the method may include confirming the position and length of the wire 348 using fluoroscopy.

Figure 32:
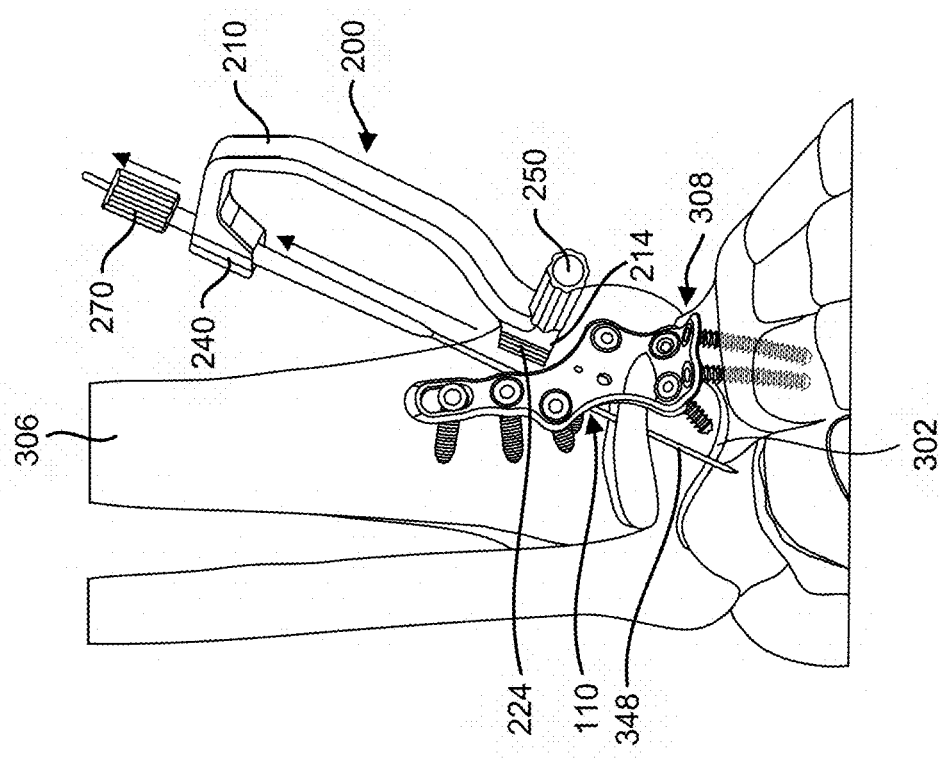
FIG. 32 is a perspective view of the bones of FIG. 31 as the alignment guide of FIG. 11 is being removed from the plate and guide wire, in accordance with an aspect of the present disclosure.
Figure 34:
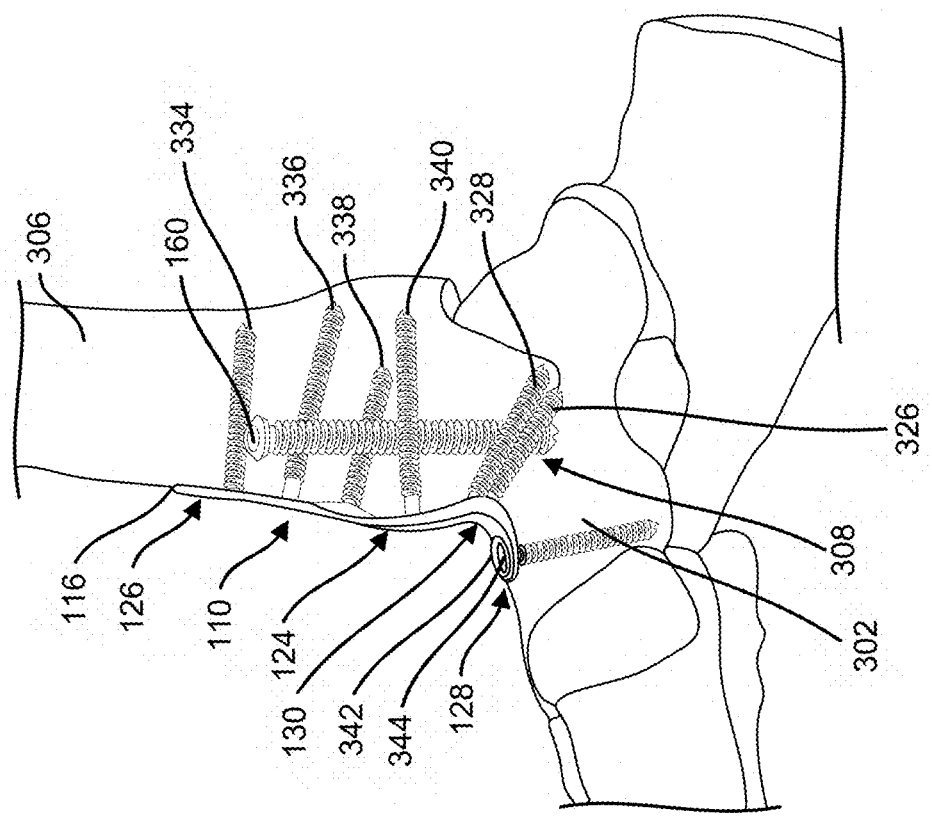
FIG. 34 is a side view of the bones of FIG. 33 after insertion of the fastener and removal of the screw driver and guide wire, in accordance with an aspect of the present disclosure.
Figure 33:
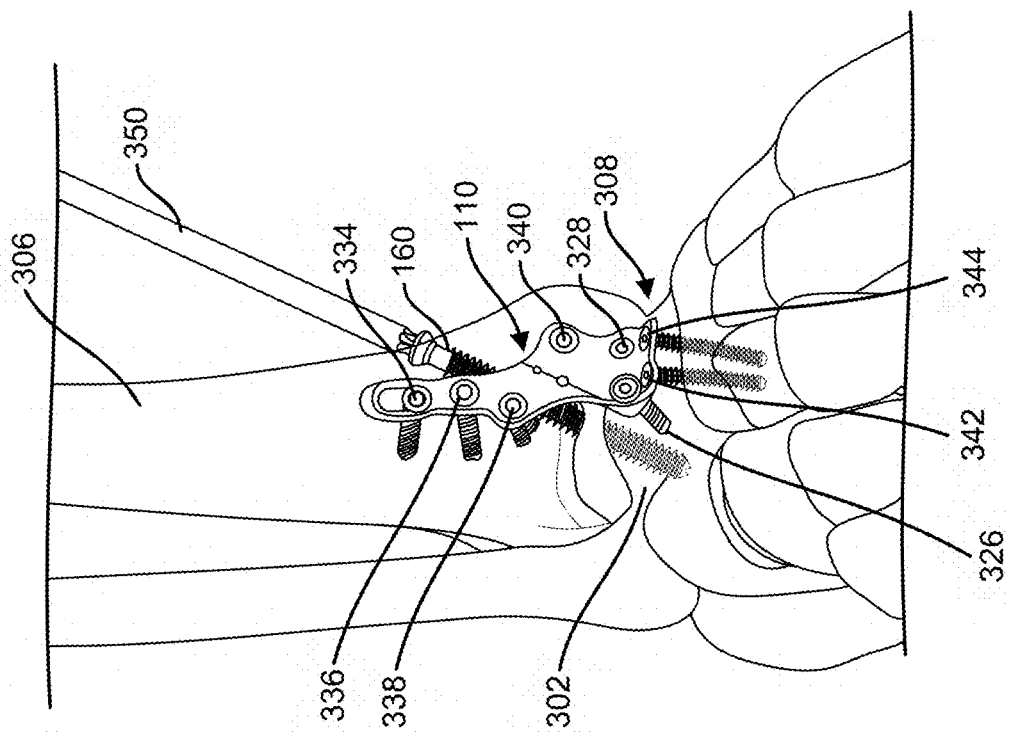
FIG. 33 is a perspective view of the bones of FIG. 32 during insertion of a fastener of the fusion system of FIG. 1 over the guide wire using a cannulated screw driver, in accordance with an aspect of the present disclosure.
Figure 35:
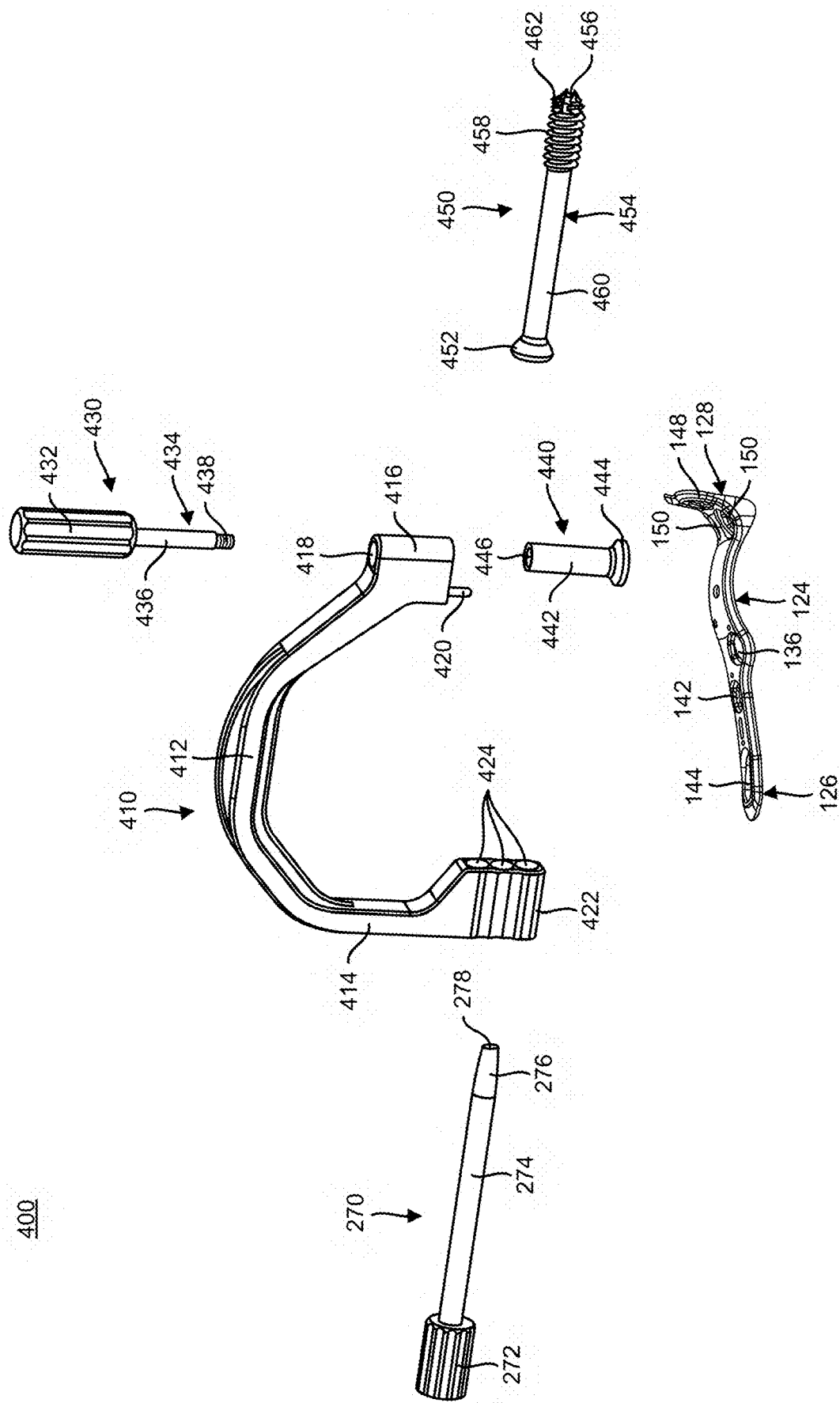
FIG. 35 is an exploded, first perspective view of another fusion system, in accordance with an aspect of the present disclosure.

Referring now to FIG. 32, once the position and length of the wire 348 is confirmed, the alignment guide 200, 410 may be removed from the plate 110. The alignment guide 200, 410 may be removed by detaching the fixation member 250, 430 from the plate 110 and sliding the tissue protector 270 and body 210, 412 off of the guide wire 348. As shown in FIG. 33, the method may then include measuring the length of the fastener 160 using a depth gauge (not shown). Next, the method includes drilling over the guide wire 348 using a drill (not shown) and inserting the fastener 160, 450 over the wire 348 and into the bones 302, 306. As shown in FIG. 34, the method may also include confirming the screw length and placement of the screws using fluoroscopy. If the screw length and placement is correct, then the guide wire 348 may be removed. Finally, the method may include performing incision closure or concomitant procedures.

As may be recognized by those of ordinary skill in the art based on the teachings herein, numerous changes and modifications may be made to the above-described and other embodiments of the present disclosure without departing from the scope of the disclosure. The components of the fusion system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the fusion system may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

Having thus described the preferred embodiments, the disclosure is now claimed to be:

1. A fusion system, comprising:
  an alignment guide system, wherein the alignment guide system comprises:
    a body, wherein the body comprises;
      an arm extending from a first end of the body to a second end of the body;
      an attachment portion coupled to the arm at the first end of the body, wherein the attachment portion comprises:
        a through hole;
        an engagement protrusion extending away from a bottom surface of the attachment portion;
        an opening extending into the attachment portion from the bottom surface;
        a first engagement surface positioned on the bottom surface of the attachment portion between the opening and a side of the attachment portion, wherein the first engagement surface comprises:
          a plurality of first protrusions; and
          a plurality of first recesses, wherein the plurality of first recesses alternate with the plurality of first protrusions; and
      an alignment portion coupled to the arm at the second end of the body;
    a fixation member engaging a first end of the body;
    a tissue protector engaging a second end of the body; and
    a rotation member with a top surface and a bottom surface, wherein the top surface of the rotation member engages a bottom surface of the attachment portion, and wherein the fixation member couples the rotation member to the attachment portion of the body; and
  an implant, wherein the alignment guide system couples to the implant.

2. The fusion system of claim 1, wherein the through hole of the attachment portion extends from a top surface of the attachment portion through to a bottom surface of the attachment portion and to a bottom surface of the engagement protrusion.

3. The fusion system of claim 1, wherein the rotation member comprises:
  a body;
  a through hole extending through the body, wherein the engagement protrusion of the attachment portion is received within the through hole of the rotation member;
  a stop pin extending away from the top surface of the rotation member, wherein the stop pin is positioned adjacent to the through hole on the top surface of the rotation member;
  an alignment pin extending away from the bottom surface of the rotation member, wherein the alignment pin is positioned adjacent to the through hole on the bottom surface of the rotation member;
  wherein the top surface of the rotation member comprises a second engagement surface between the alignment pin and a side of the rotation member, wherein the second engagement surface comprises:
    a plurality of second protrusions; and
    a plurality of second recesses, wherein the plurality of second recesses alternate with the plurality of second protrusions.

4. The fusion system of claim 3, wherein the stop pin engages the opening of the attachment portion when the rotation member engages the attachment portion.

5. The fusion system of claim 3, wherein a first end of each first protrusion of the plurality of first protrusions is spaced apart a first distance and a second end of each first protrusion of the plurality of first protrusions is spaced apart a second distance, and wherein the first distance is smaller than the second distance; and
  wherein a first end of each second recess of the plurality of second recesses is spaced apart a third distance and a second end of each second recess of the plurality of second recesses is spaced apart a fourth distance, and wherein the third distance is smaller than the fourth distance.

6. The fusion system of claim 3, wherein the plurality of first protrusions are positioned to form at least one of a curved or arced shape; and
  wherein the plurality of second recesses are positioned to form at least one of a curved or arced shape.

7. The fusion system of claim 1, wherein the alignment portion comprises:
  at least one hole extending through the alignment portion from a first end to a second end.

8. The fusion system of claim 7, wherein the at least one hole is three holes.

9. The fusion system of claim 7, wherein the fixation member comprises:
  a knob; and
  a shaft extending away from the knob, wherein the shaft comprises:
    a first portion coupled to and extending away from a second end of the knob;

a second portion coupled to and extending away from the first portion, wherein the first portion includes a first diameter, the second portion includes a second diameter, and the first diameter is larger than the second diameter;

a first engagement member coupled to and extending away from the second portion; and a second engagement member coupled to and extending away from the first engagement member, wherein the first engagement member includes a third diameter, the second engagement member includes a fourth diameter, and the third diameter is larger than the second diameter;

wherein the first engagement member is threaded to engage threads in the through hole of the rotation member and the second engagement member is threaded to engage threads in an engagement opening in the implant.

10. The fusion system of claim 9, wherein the tissue protector comprises:
a handle portion;
a shaft portion coupled to and extends from the handle portion;
a tip at a second end of the shaft portion; and
a through hole extending through the handle portion and shaft portion along a longitudinal axis of the tissue protector;
wherein the tissue protector is configured to extends through the at least one hole of the alignment portion of the alignment guide system.

11. The fusion system of claim 10, wherein the implant comprises:
a body portion;
an extension portion extending away from a first end of the body portion;
a curved portion extending away from a second end of the body portion;
a foot member extending away from the curved portion perpendicular to the body portion; and
a fastener, wherein the fastener engages the alignment guide system to position the fastener relative to the body portion of the implant.

12. The fusion system of claim 11, wherein the body portion comprises:
at least one first through hole;
an engagement opening for receiving a portion of the fixation member; and
an alignment opening spaced diagonally from the engagement opening, wherein the alignment opening receives an alignment pin of the rotation member.

13. The fusion system of claim 12, wherein the extension portion comprises:
at least one second through hole; and
a compression slot positioned near a first end of the implant;
wherein the at least one second through hole is positioned between the compression slot and the body portion.

14. The fusion system of claim 13, wherein the curved portion comprises:
at least one third through hole extending through the implant at an angle relative to a top surface of the implant.

15. The fusion system of claim 14, wherein the foot member comprises:
at least one fourth through hole extending through the implant perpendicular to the top surface of the implant.

16. The fusion system of claim 11, wherein the fastener comprises:
a head portion;
a shaft portion extending away from the head portion, wherein at least part of the shaft portion is threaded; and
a cannulation extending from a first end to a second end of the fastener to engage a guide wire of the alignment guide system.

17. A fusion system, comprising:
an implant; and
an alignment guide system, comprising:
a body, wherein the body comprises:
an arm extending from a first end of the body to a second end of the body;
an attachment portion coupled to the arm at the first end of the body, wherein the attachment portion comprises:
a through hole extending from a top surface of the attachment portion through to a bottom surface of the attachment portion; and
an alignment portion coupled to the arm at the second end of the body, wherein the alignment portion comprises:
at least one hole extending through the alignment portion from a first end to a second end;
a fixation member engaging the first end of the body, wherein the fixation member comprises:
a knob; and
a shaft extending away from the knob, wherein the shaft comprises:
a first portion coupled to and extending away from a second end of the knob;
a second portion coupled to and extending away from the first portion, wherein the first portion includes a first diameter, the second portion includes a second diameter, and the first diameter is larger than the second diameter;
a first engagement member coupled to and extending away from the second portion; and
a second engagement member coupled to and extending away from the first engagement member, wherein the first engagement member includes a third diameter, the second engagement member includes a fourth diameter, and the third diameter is larger than the second diameter;
wherein the first engagement member is threaded to engage threads in a through hole of a rotation member and the second engagement member is threaded to engage threads in an engagement opening in the implant;
a tissue protector engaging the second end of the body; and
wherein the alignment guide system couples to the implant.

18. The fusion system of claim 17, wherein the tissue protector comprises:
a handle portion;
a shaft portion coupled to and extends from the handle portion;
a tip at a second end of the shaft portion; and
a through hole extending through the handle portion and the shaft portion along a longitudinal axis of the tissue protector;

wherein the tissue protector extends through the at least one hole of the alignment portion of the alignment guide system;
wherein the implant comprises:
  a body portion, comprising:
    at least one first through hole;
    an engagement opening for receiving a portion of the fixation member; and
    an alignment opening spaced diagonally from the engagement opening, wherein the alignment opening receives an alignment pin of a rotation member;
  an extension portion extending away from a first end of the body portion, wherein the extension portion comprises:
    at least one second through hole; and
    a compression slot positioned near a first end of the implant;
    wherein the at least one second through hole is positioned between the compression slot and the body portion;
  a curved portion extending away from a second end of the body portion; and
  a foot member extending away from the curved portion perpendicular to the body portion.

19. The fusion system of claim 18, further comprising:
a fastener, wherein the fastener engages the alignment guide system to position the fastener relative to the implant, and wherein the fastener comprises:
  a head portion;
  a shaft portion extending away from the head portion, wherein at least part of the shaft portion is threaded; and
  an opening extending from a first end to a second end of the fastener to engage a guide wire of the alignment guide system.

* * * * *